United States Patent
Miller et al.

(10) Patent No.: US 10,980,542 B2
(45) Date of Patent: Apr. 20, 2021

(54) CIRCULAR SURGICAL STAPLER WITH RECESSED DECK

(71) Applicant: Ethicon Endo-Surgery, LLC, Guaynabo, PR (US)

(72) Inventors: Christopher C. Miller, Loveland, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 530 days.

(21) Appl. No.: 15/350,513

(22) Filed: Nov. 14, 2016

(65) Prior Publication Data

US 2018/0132853 A1    May 17, 2018

(51) Int. Cl.
*A61B 17/115*      (2006.01)
*A61B 17/072*      (2006.01)
(Continued)

(52) U.S. Cl.
CPC .... *A61B 17/1155* (2013.01); *A61B 17/07207* (2013.01); *A61B 2017/00199* (2013.01); *A61B 2017/00398* (2013.01); *A61B 2017/00734* (2013.01); *A61B 2017/07228* (2013.01); *A61B 2017/07257* (2013.01);
(Continued)

(58) Field of Classification Search
CPC .............. A61B 17/1155; A61B 17/115; A61B 17/1152; A61B 17/07207; A61B 17/068; A61B 17/072; A61B 2017/07271; A61B 2017/2905; A61B 2017/00734; A61B 2017/00398; A61B 2017/00199; A61B 2017/07228; A61B 2017/1157; A61B 2017/07221; A61B 2017/07235; A61B 2017/07242; A61B 2017/07264

USPC ..... 227/179.1, 176.1, 180.1, 175.1; 606/219, 606/137; 206/339
See application file for complete search history.

(56) References Cited

U.S. PATENT DOCUMENTS

| | | | |
|---|---|---|---|
| 5,205,459 | A | 4/1993 | Brinkerhoff et al. |
| 5,271,544 | A | 12/1993 | Fox et al. |

(Continued)

FOREIGN PATENT DOCUMENTS

| | | |
|---|---|---|
| CN | 3657881 | 6/2007 |
| CN | 3657882 | 6/2007 |

(Continued)

OTHER PUBLICATIONS

European Search Report and Written Opinion dated Apr. 18, 2018 for Application No. EP 17201266.8, 7 pgs.

(Continued)

*Primary Examiner* — Valentin Neacsu
(74) *Attorney, Agent, or Firm* — Frost Brown Todd LLC

(57) ABSTRACT

An apparatus includes a body, a shaft assembly, a stapling head assembly, and an anvil. The stapling head assembly includes a deck member, a plurality of staples, and a driver. The deck member includes a deck surface, an outer annular array of staple openings formed through the deck surface, an inner annular array of staple openings formed through the deck surface, and a plurality of recesses formed in the deck surface. At least a portion of the recesses are positioned between at least some of the staple openings. The driver is operable to drive the staples through the staple openings. The anvil is operable to compress tissue against the deck surface.

20 Claims, 18 Drawing Sheets

(51) Int. Cl.
*A61B 17/29* (2006.01)
*A61B 17/00* (2006.01)
*A61B 90/00* (2016.01)

(52) U.S. Cl.
CPC .............. *A61B 2017/07271* (2013.01); *A61B 2017/07278* (2013.01); *A61B 2017/2905* (2013.01); *A61B 2090/0811* (2016.02)

(56) References Cited

U.S. PATENT DOCUMENTS

| | | | |
|---|---|---|---|
| 5,275,322 A | 1/1994 | Wolf et al. | |
| 5,285,945 A | 2/1994 | Brinkerhoff et al. | |
| 5,292,053 A | 3/1994 | Smith et al. | |
| 5,333,773 A | 8/1994 | Main et al. | |
| 5,350,104 A | 9/1994 | Main et al. | |
| 5,533,661 A | 7/1996 | Main et al. | |
| 6,978,922 B2 * | 12/2005 | Bilotti .................. | A61B 17/115 227/176.1 |
| 7,168,604 B2 | 1/2007 | Milliman et al. | |
| RE39,841 E * | 9/2007 | Bilotti .................. | A61B 17/115 227/176.1 |
| 7,364,060 B2 | 4/2008 | Milliman | |
| 7,546,940 B2 | 6/2009 | Milliman et al. | |
| 7,794,475 B2 | 9/2010 | Hess et al. | |
| 8,157,152 B2 * | 4/2012 | Holsten ............ | A61B 17/00491 227/176.1 |
| 8,328,062 B2 * | 12/2012 | Viola .................. | A61B 17/115 227/179.1 |
| 8,408,441 B2 | 4/2013 | Wenchell et al. | |
| 8,413,870 B2 * | 4/2013 | Pastorelli ............ | A61B 17/1114 227/179.1 |
| 8,453,906 B2 | 6/2013 | Huang et al. | |
| 8,613,383 B2 | 12/2013 | Beckman et al. | |
| D700,325 S | 2/2014 | Nalagatla et al. | |
| 8,657,176 B2 * | 2/2014 | Shelton, IV ..... | A61B 17/00491 227/178.1 |
| 8,684,252 B2 | 4/2014 | Patel et al. | |
| 8,746,531 B2 | 6/2014 | Wenchell et al. | |
| 8,794,497 B2 | 8/2014 | Zingman | |
| 8,910,847 B2 | 12/2014 | Nalagatla et al. | |
| 9,022,274 B2 | 5/2015 | Penna | |
| 9,033,204 B2 * | 5/2015 | Shelton, IV ....... | A61B 17/1155 227/179.1 |
| 9,038,882 B2 | 5/2015 | Racenet et al. | |
| 9,055,942 B2 | 6/2015 | Balbierz et al. | |
| 9,168,042 B2 | 10/2015 | Milliman | |
| 9,186,141 B2 | 11/2015 | Williams | |
| 9,289,207 B2 | 3/2016 | Shelton, IV | |
| 9,351,724 B2 | 5/2016 | Penna | |
| 9,463,022 B2 | 10/2016 | Swayze et al. | |
| 9,498,222 B2 | 11/2016 | Scheib et al. | |
| 9,532,783 B2 | 1/2017 | Swayze et al. | |
| 9,572,573 B2 | 2/2017 | Scheib et al. | |
| 9,597,083 B2 | 3/2017 | Penna | |
| 9,757,133 B2 | 9/2017 | Latimer et al. | |
| 9,801,626 B2 * | 10/2017 | Parihar ............. | A61B 17/1155 |
| 9,867,619 B2 | 1/2018 | Williams | |
| 10,080,566 B2 | 9/2018 | Milliman | |
| D830,550 S | 10/2018 | Miller et al. | |
| D833,010 S | 11/2018 | Harris et al. | |
| D833,608 S | 11/2018 | Miller et al. | |
| D837,373 S | 1/2019 | Miller et al. | |
| 10,213,203 B2 | 2/2019 | Swayze et al. | |
| 10,245,040 B2 * | 4/2019 | Milliman ............... | A61B 90/98 |
| 10,271,841 B2 | 4/2019 | Overmyer et al. | |
| 10,271,850 B2 | 4/2019 | Williams | |
| 10,271,851 B2 | 4/2019 | Shelton, IV et al. | |
| 10,285,701 B2 | 5/2019 | Prior | |
| 10,456,140 B2 | 10/2019 | Shelton, IV et al. | |
| 10,492,790 B2 | 12/2019 | DiNardo et al. | |
| 10,499,909 B2 | 12/2019 | Scheib et al. | |
| 2003/0178465 A1 * | 9/2003 | Bilotti .................. | A61B 17/115 227/180.1 |
| 2007/0060952 A1 | 3/2007 | Roby et al. | |
| 2007/0131732 A1 * | 6/2007 | Holsten ............ | A61B 17/00491 227/179.1 |
| 2007/0175963 A1 * | 8/2007 | Bilotti .................. | A61B 17/115 227/179.1 |
| 2009/0001126 A1 * | 1/2009 | Hess ...................... | A61B 17/32 227/176.1 |
| 2010/0108740 A1 * | 5/2010 | Pastorelli ............ | A61B 17/1114 227/178.1 |
| 2011/0011916 A1 * | 1/2011 | Levine .................. | A61B 17/115 227/179.1 |
| 2011/0017800 A1 * | 1/2011 | Viola .................. | A61B 17/115 227/175.1 |
| 2012/0016413 A1 | 1/2012 | Timm et al. | |
| 2012/0080488 A1 * | 4/2012 | Shelton, IV ..... | A61B 17/00491 227/176.1 |
| 2012/0083836 A1 * | 4/2012 | Shelton, IV ..... | A61B 17/00491 606/219 |
| 2012/0168487 A1 * | 7/2012 | Holsten ............ | A61B 17/00491 227/176.1 |
| 2012/0241505 A1 * | 9/2012 | Alexander, III ............ | A61B 17/00491 227/179.1 |
| 2013/0026209 A1 * | 1/2013 | Mozdzierz ......... | A61B 17/1155 227/180.1 |
| 2014/0097224 A1 * | 4/2014 | Prior .................... | A61B 17/068 227/176.1 |
| 2014/0151430 A1 * | 6/2014 | Scheib ............... | A61B 17/1155 227/175.1 |
| 2014/0158747 A1 | 6/2014 | Measamer et al. | |
| 2014/0166726 A1 * | 6/2014 | Schellin ........... | A61B 17/07292 227/178.1 |
| 2014/0166728 A1 | 6/2014 | Swayze et al. | |
| 2015/0014393 A1 * | 1/2015 | Milliman ............... | A61B 90/98 227/180.1 |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |
| 2015/0297233 A1 * | 10/2015 | Huitema ............... | A61B 17/068 227/176.1 |
| 2015/0297236 A1 * | 10/2015 | Harris ................. | A61B 17/0644 227/176.1 |
| 2016/0089147 A1 * | 3/2016 | Harris ................. | A61B 17/0684 227/176.1 |
| 2016/0089149 A1 * | 3/2016 | Harris ................. | A61B 17/0644 227/176.1 |
| 2016/0100837 A1 | 4/2016 | Huang et al. | |
| 2016/0113653 A1 | 4/2016 | Zingman | |
| 2016/0374665 A1 | 12/2016 | DiNardo et al. | |
| 2016/0374666 A1 | 12/2016 | DiNardo et al. | |
| 2016/0374672 A1 | 12/2016 | Bear et al. | |
| 2017/0056000 A1 * | 3/2017 | Nalagatla ............. | A61B 17/068 |
| 2017/0258471 A1 | 9/2017 | DiNardo et al. | |
| 2017/0281169 A1 | 10/2017 | Harris et al. | |
| 2020/0305881 A1 | 10/2020 | DiNardo et al. | |

FOREIGN PATENT DOCUMENTS

| | | |
|---|---|---|
| EP | 1 316 290 A2 | 6/2003 |
| EP | 2 719 341 A1 | 4/2014 |
| JP | S53-148190 A | 12/1978 |
| JP | 2003-199749 A | 7/2003 |
| JP | 2007-209751 A | 8/2007 |
| JP | 2008-212672 A | 9/2008 |
| JP | 2012-024574 A | 2/2012 |
| JP | 1481409 S | 10/2013 |
| JP | 1594729 S | 1/2018 |

OTHER PUBLICATIONS

European Exam Report dated Jan. 23, 2019 for Application No. EP 17201266.8, 3 pgs.
International Search Report and Written Opinion dated Aug. 22, 2017 for Application No. PCT/US2017/035104, 9 pgs.
Design U.S. Appl. No. 29/660,436, filed Aug. 21, 2018 by Miller et al., entitled: Surgical Stapler.

(56) References Cited

OTHER PUBLICATIONS

Design U.S. Appl. No. 29/665,182, filed Oct. 1, 2018 by Miller et al., entitled: Stapling Head Feature for Surgical Stapler.
Design U.S. Appl. No. 29/672,408, filed Dec. 5, 2018 by Miller et al., entitled: Surgical Stapler.
U.S. Appl. No. 14/864,310, filed Sep. 24, 2015.
U.S. Appl. No. 15/350,593, filed Nov. 14, 2016.
U.S. Appl. No. 15/350,621, filed Nov. 14, 2016.
U.S. Appl. No. 15/350,624, filed Nov. 14, 2016.
Japanese Office Action, Notification, dated Mar. 13, 2018 for Application No. JP 2017-010286, 2 pgs.
Japanese Office Action, Notification, dated Aug. 7, 2018 for Application No. JP 2017-010287, 2 pgs.
Japanese Office Action, Notification, dated Mar. 13, 2018 for Application No. JP 2017-023542, 2 pgs.
Japanese Office Action, Notification, dated Mar. 13, 2018 for Application No. JP 2017-023544, 2 pgs.
Japanese Office Action, Notification, dated Mar. 13, 2018 for Application No. JP 2017-023545, 2 pgs.
Japanese Office Action, Notification, dated Mar. 13, 2018 for Application No. JP 2017-023652, 2 pgs.
Japanese Office Action, Notification, dated Mar. 13, 2018 for Application No. JP 2017-023654, 2 pgs.
Japanese Office Action, Notification, dated Mar. 13, 2018 for Application No. JP 2017-023655, 2 pgs.
Japanese Office Action, Notification, dated Mar. 13, 2018 for Application No. JP 2017-023656, 2 pgs.
Japanese Office Action, Notification, dated Aug. 7, 2018 for Application No. JP 2017-023649, 1 pg.
Japanese Office Action, Notification, dated Aug. 7, 2018 for Application No. JP. 2017-023651, 1 pg.
Japanese Office Action, Notification, dated Aug. 7, 2018 for Application No. JP 2017-023653, 1 pg.
U.S. Appl. No. 16/994,101, filed Aug. 14, 2020, by Miller et al., entitled: "Staple Forming Pocket Configurations for Circular Surgical Stapler Anvil.".

* cited by examiner

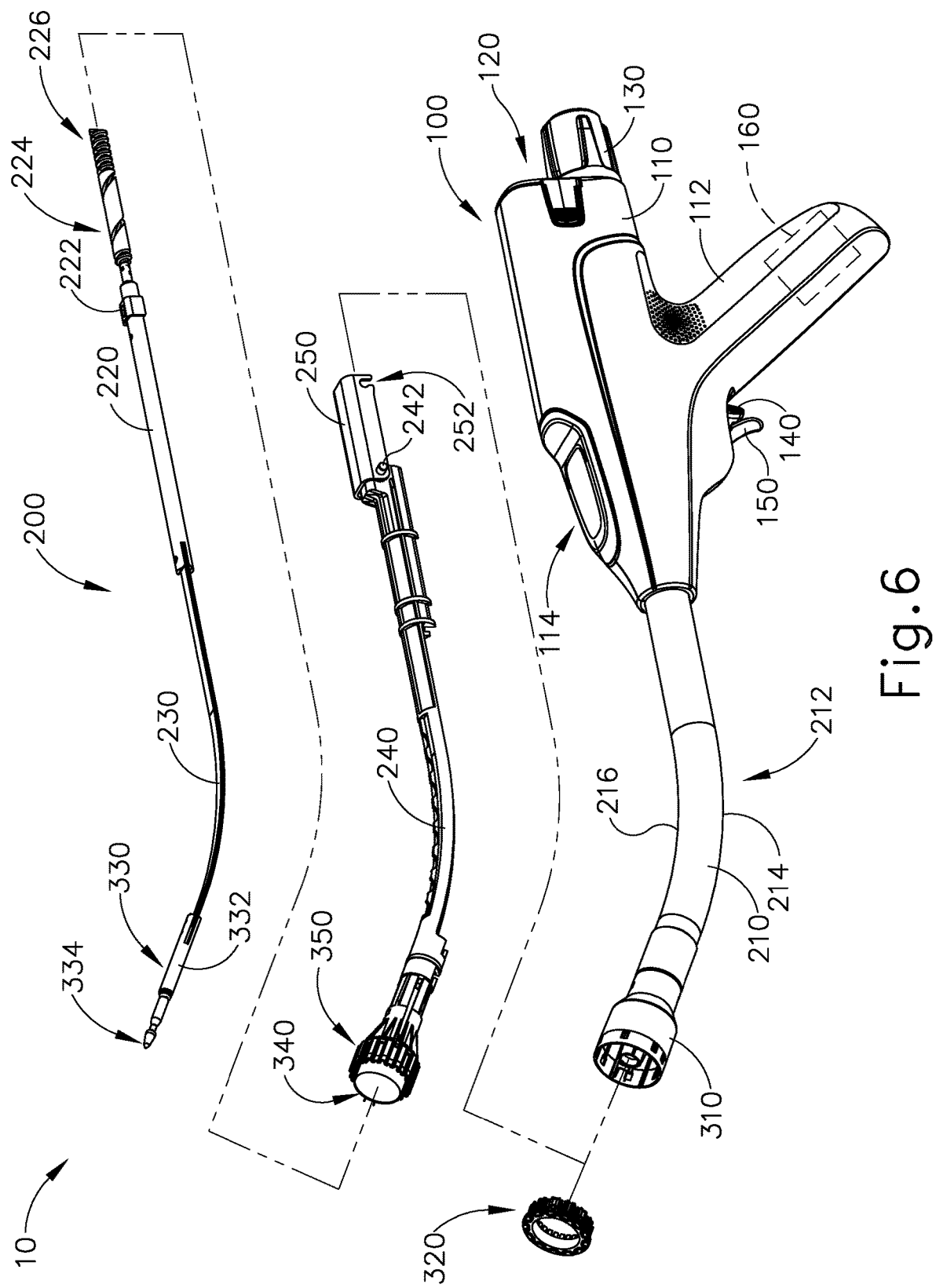

CIRCULAR SURGICAL STAPLER WITH RECESSED DECK

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts an exploded perspective view of the circular stapler of FIG. 1, with portions of the shaft assembly shown separately from each other;

Figure 1:
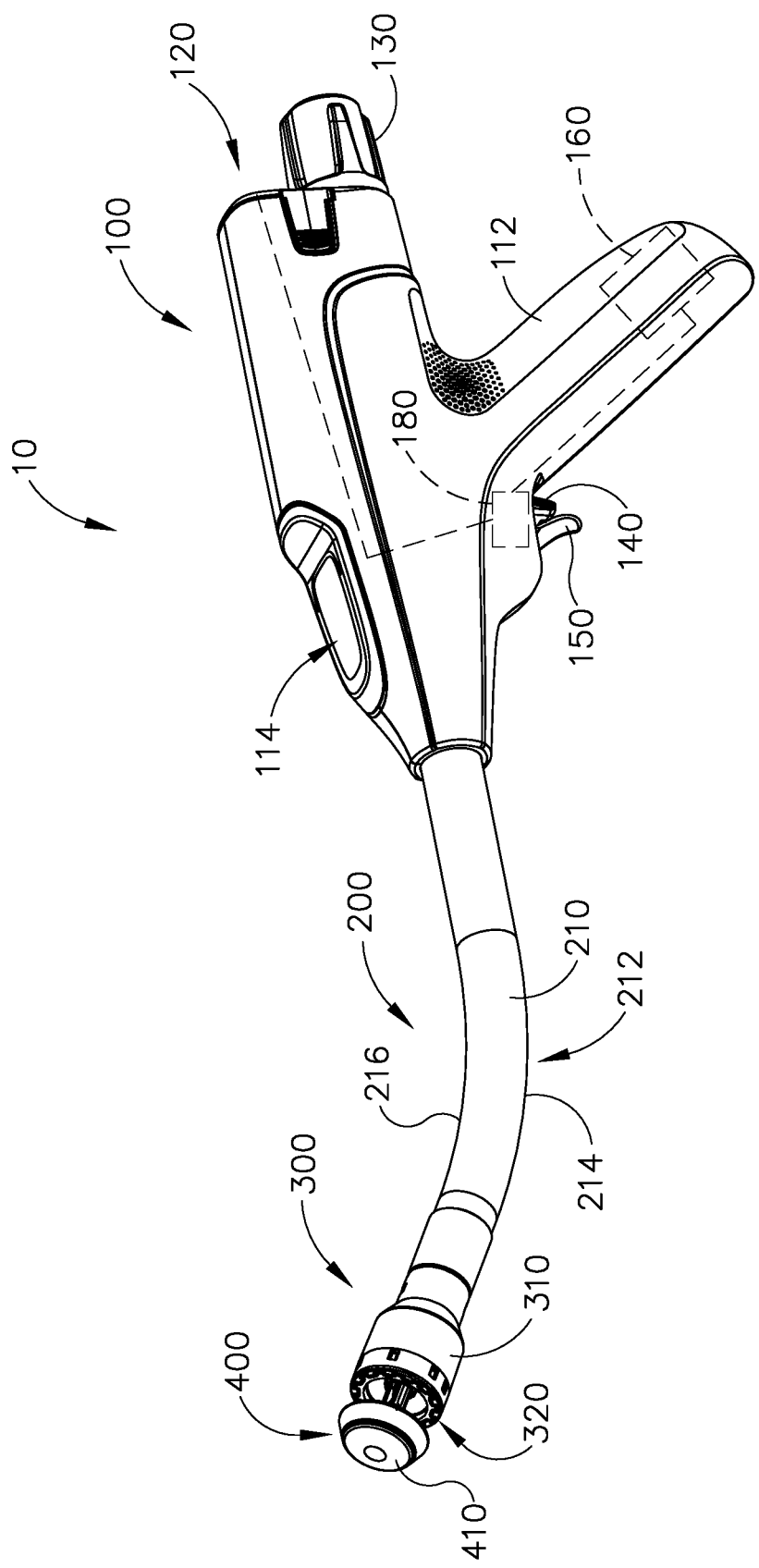
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
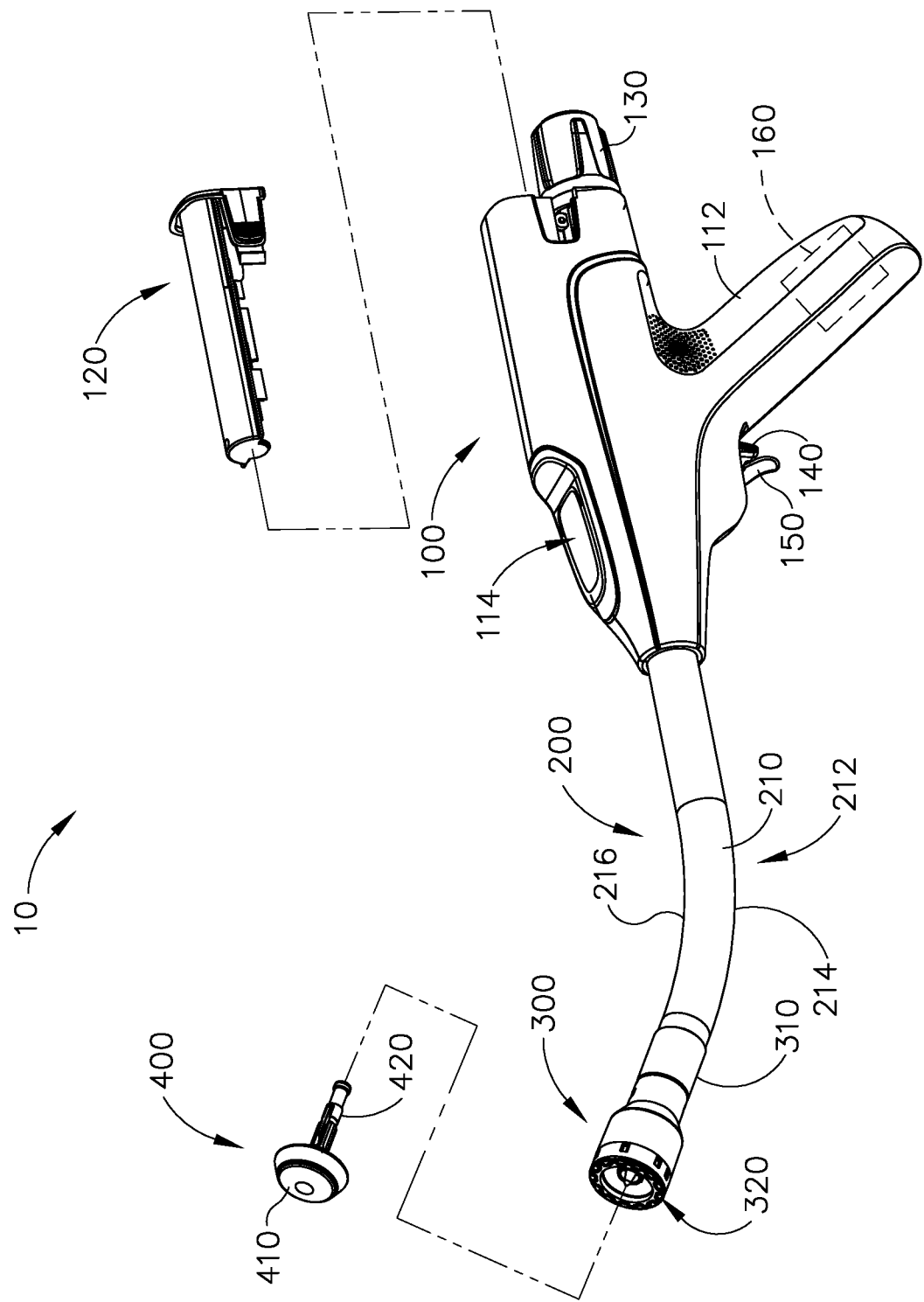
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), an anvil (400), and a removable battery pack (120). Each of these components will be described in greater detail below. It should be understood that, in addition to or in lieu of the following, instrument (10) may be further constructed and operable in accordance with at least some of the teachings of U.S. patent application Ser. No. 14/751,612, entitled "Method of Applying an Annular Array of Staples to Tissue," filed Jun. 26, 2015, issued as U.S. Pat. No. 10,478,189 on Nov. 19, 2019; U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

A. Exemplary Tissue Engagement Features of Circular Stapling Instrument

Figure 3:
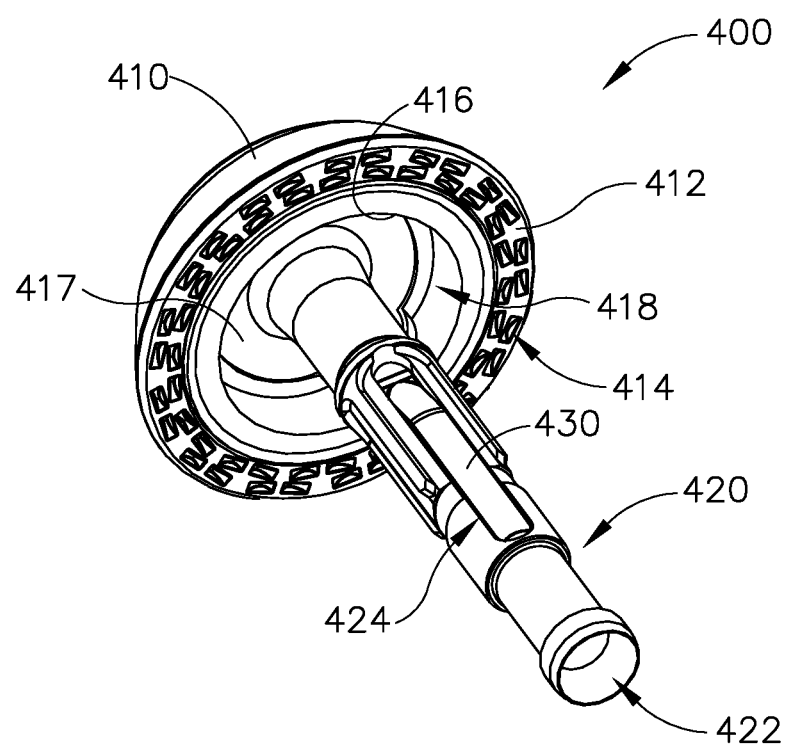
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Figure 4:
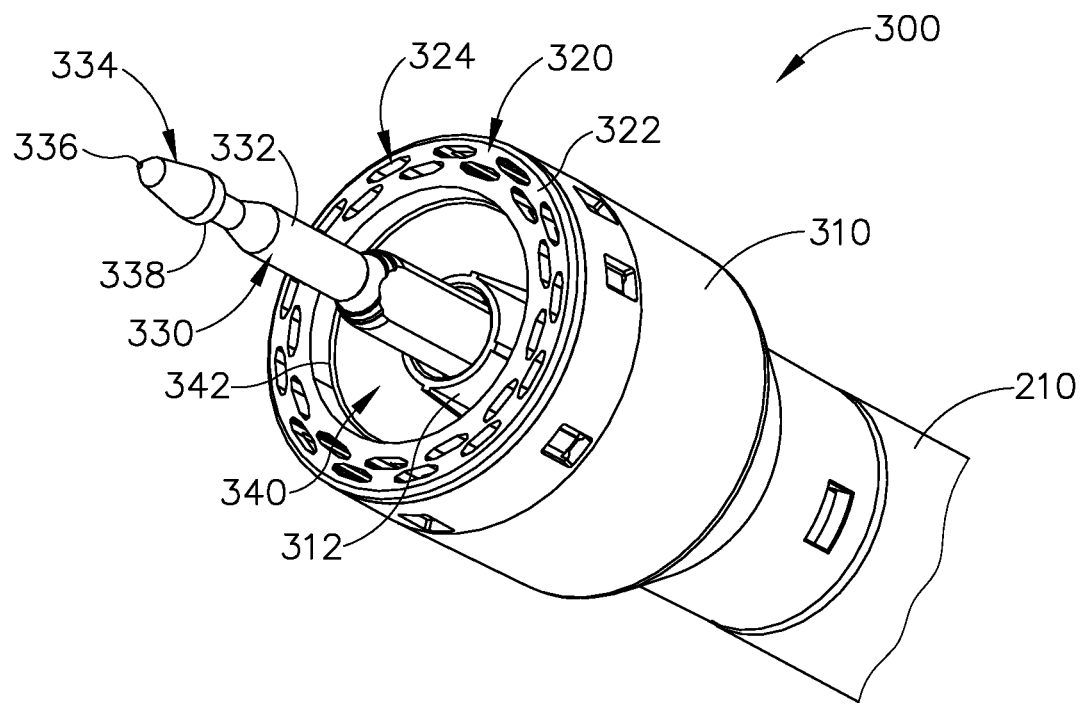
FIG. 4 depicts a perspective view of the stapling head assembly of the circular stapler of FIG. 1.
Figure 5:
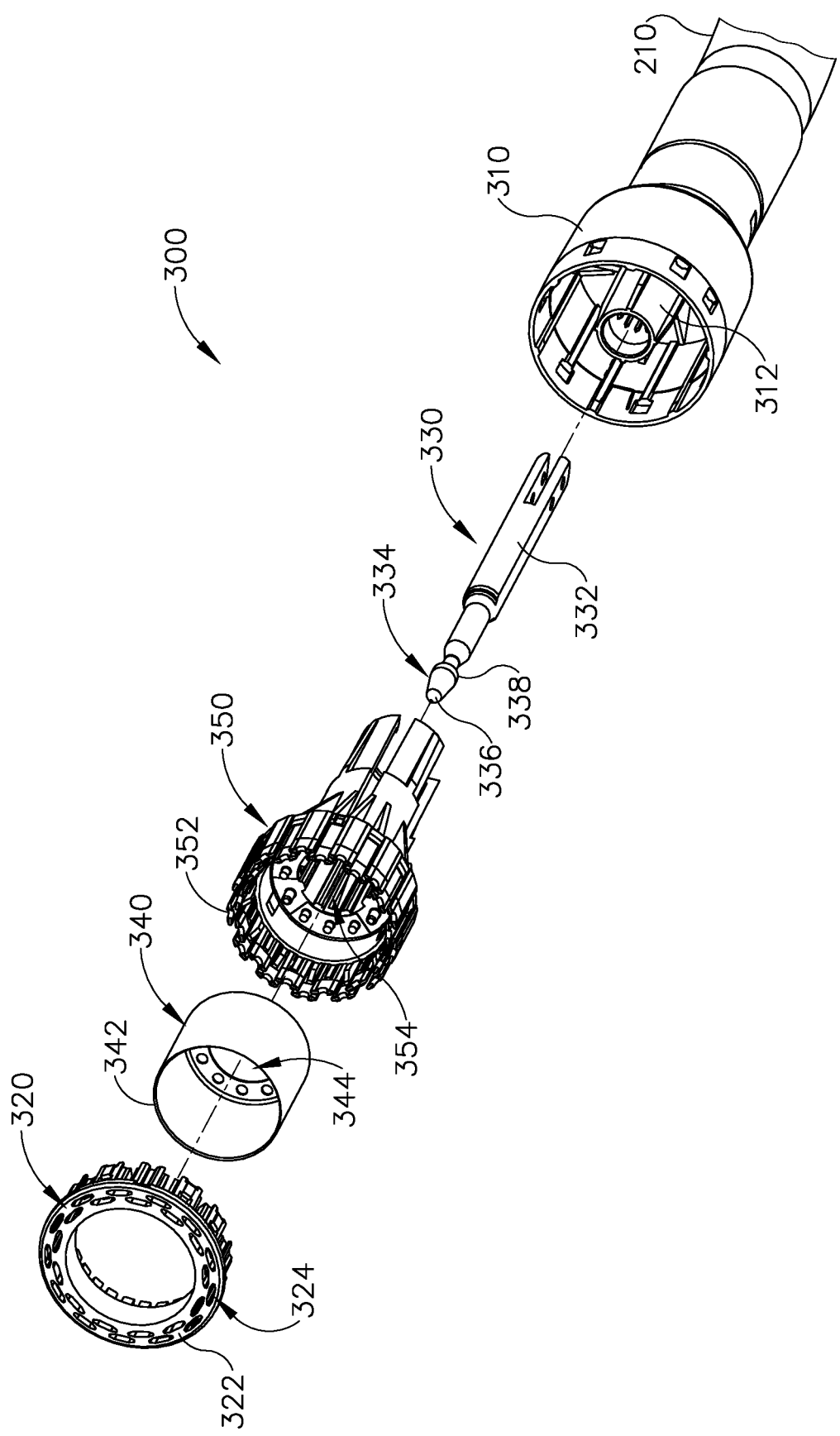
FIG. 5 depicts an exploded perspective view of the stapling head assembly of FIG. 4.

Stapling head assembly (300) is located at the distal end of shaft assembly (200). As shown in FIGS. 1-2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4-5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (420). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Deck member (320) defines an inner diameter that is just slightly larger than the outer diameter defined by knife member (340). Deck member (320) is thus configured to allow knife member (340) to translate distally to a point where cutting edge (342) is distal to deck surface (322).

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section (212) that is configured to facilitate positioning of stapling head assembly (300) within a patient's colon as described below. Curved section (212) includes an inner curve (216) and an outer curve (214).

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

B. Exemplary User Input Features of Circular Stapling Instrument

As shown in FIG. 1, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (500) away from stapling head assembly (300). Knob (130) may thus be used to adjust the gap distance between opposing surfaces (412, 322) of anvil (400) and stapling head assembly (300) until a suitable gap distance has been achieved.

In the present example, handle assembly (100) comprises a user feedback feature (114) that is configured to provide the operator with visual feedback indicating the positioning of anvil (400) in relation to stapling assembly (300). The operator may thus observe user feedback feature (114) while rotating knob (130), to confirm whether the suitable gap distance between anvil (400) and stapling assembly (300) has been achieved. By way of example only, user feedback feature (114) may be configured and operable in accordance with at least some of the teachings of U.S. patent application Ser. No. 14/751,612, entitled "Method of Applying an Annular Array of Staples to Tissue," filed Jun. 26, 2015, issued as U.S. Pat. No. 10,478,189 on Nov. 19, 2019, the disclosure of which is incorporated by reference herein. Other suitable forms of providing user feedback will be apparent to those of ordinary skill in the art in view of the teachings herein.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range.

In the present example, firing trigger (150) of the present example includes an integral actuation paddle, such as the paddle shown and described in U.S. patent application Ser. No. 14/751,231, entitled "Surgical Stapler with Reversible Motor," filed Jun. 26, 2015, issued as U.S. Pat. No. 10,456,134 on Oct. 29, 2019, the disclosure of which is incorporated by reference herein. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) as described in greater detail below.

Battery pack (120) is operable to provide electrical power to a motor (160) as noted above. Battery pack (120) may be removably coupled with handle assembly (100) through a snap fit or in any other suitable fashion. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery back (120) cannot be removed from handle assembly (100).

C. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
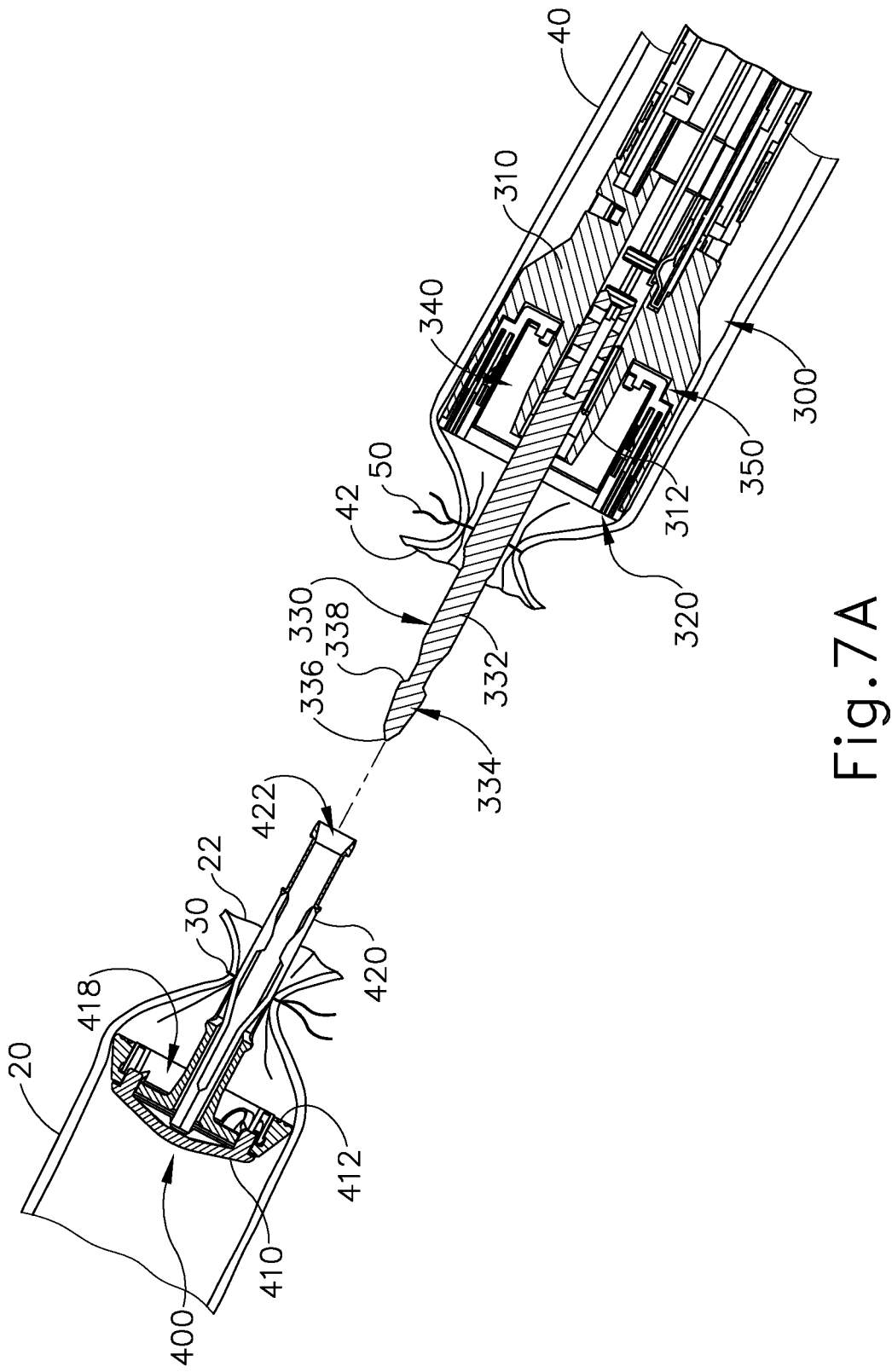
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. By way of example only, the surgical procedure may be performed laparoscopically in accordance with at least some of the teachings of U.S. Pub. No. 2016/0100837, entitled "Staple Cartridge," published Apr. 14, 2016, issued as U.S. Pat. No. 10,076,325 on Sep. 18, 2018, the disclosure of which is incorporated by reference herein; and/or U.S. patent application Ser. No. 14/864,310, entitled "Apparatus and Method for Forming a Staple Line with Trocar Passageway," filed Sep. 24, 2015, issued as U.S. Pat. No. 10,485,548 on Nov. 26, 2019, the disclosure of which is incorporated by reference herein. Various other suitable ways in which instrument (10) may be used to form an anastomosis (70) in a laparoscopic procedure will be apparent to those of ordinary skill in the art in view of the teachings herein.

As shown in FIG. 7A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Figure 7B:
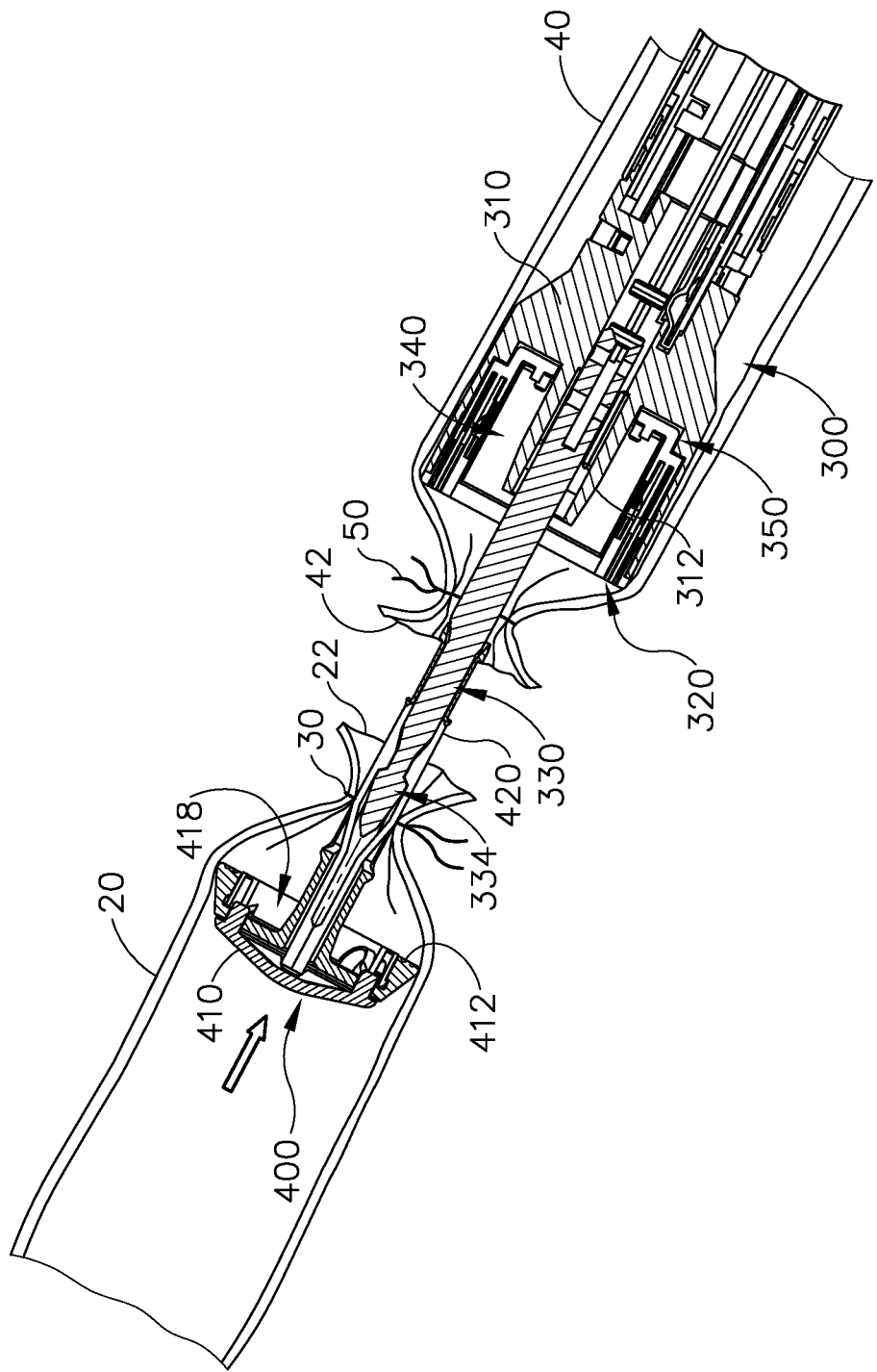
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
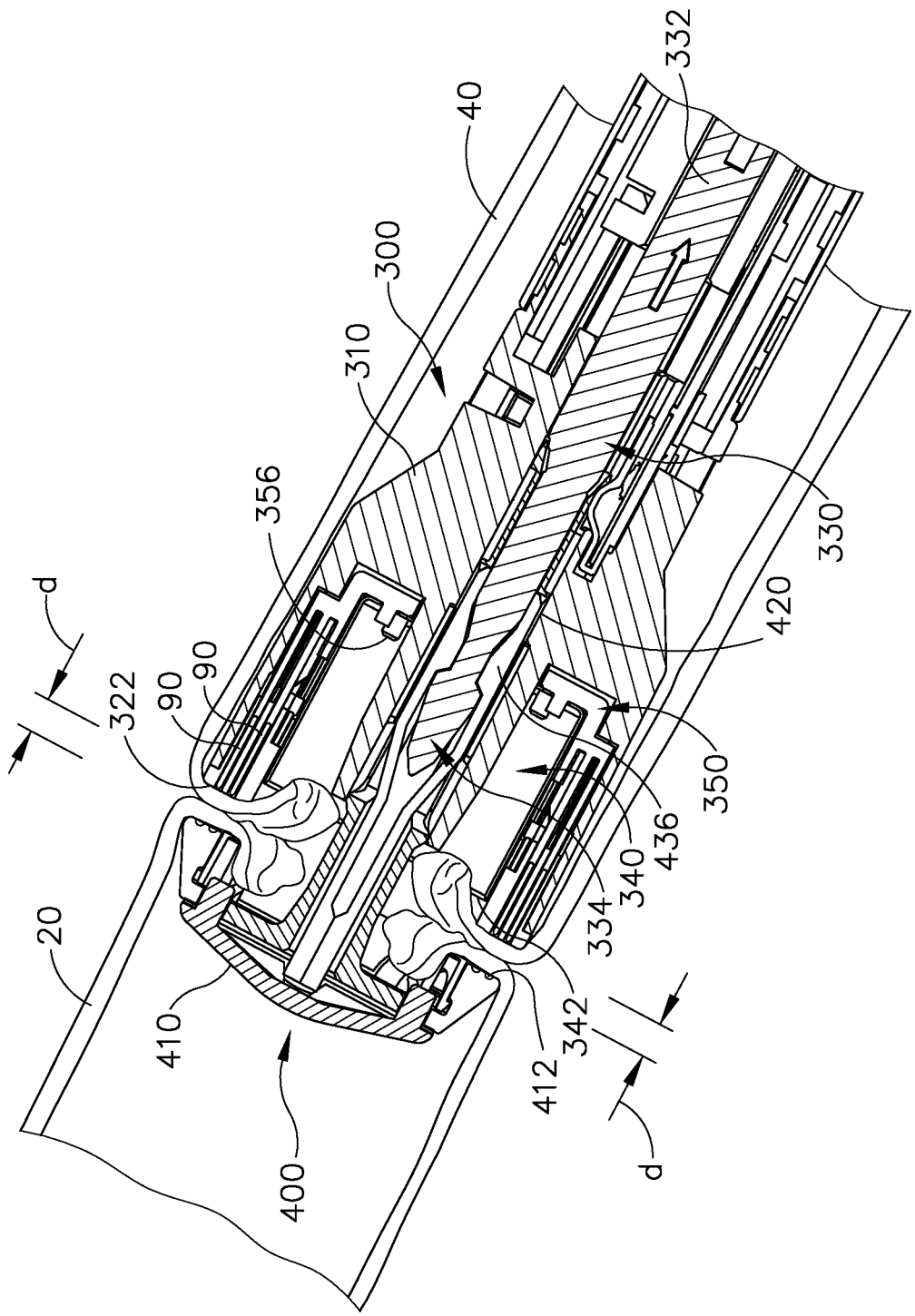
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding handle assembly (100) stationary via pistol grip (112). This rotation of knob (130) causes trocar (330) and anvil (400) to retract proximally, as described above. As shown in FIG. 7C, this proximal retraction of trocar (330) and anvil (400) compresses the tissue of tubular anatomical structures (20, 40) between surfaces (412, 322) of anvil (400) and stapling head assembly (300). The operator observes user feedback feature (114) to determine whether the gap distance (d) between opposing surfaces (412, 322) of anvil (400) and stapling head assembly (300) is appropriate; and makes any necessary adjustments via knob (130).

Figure 7D:
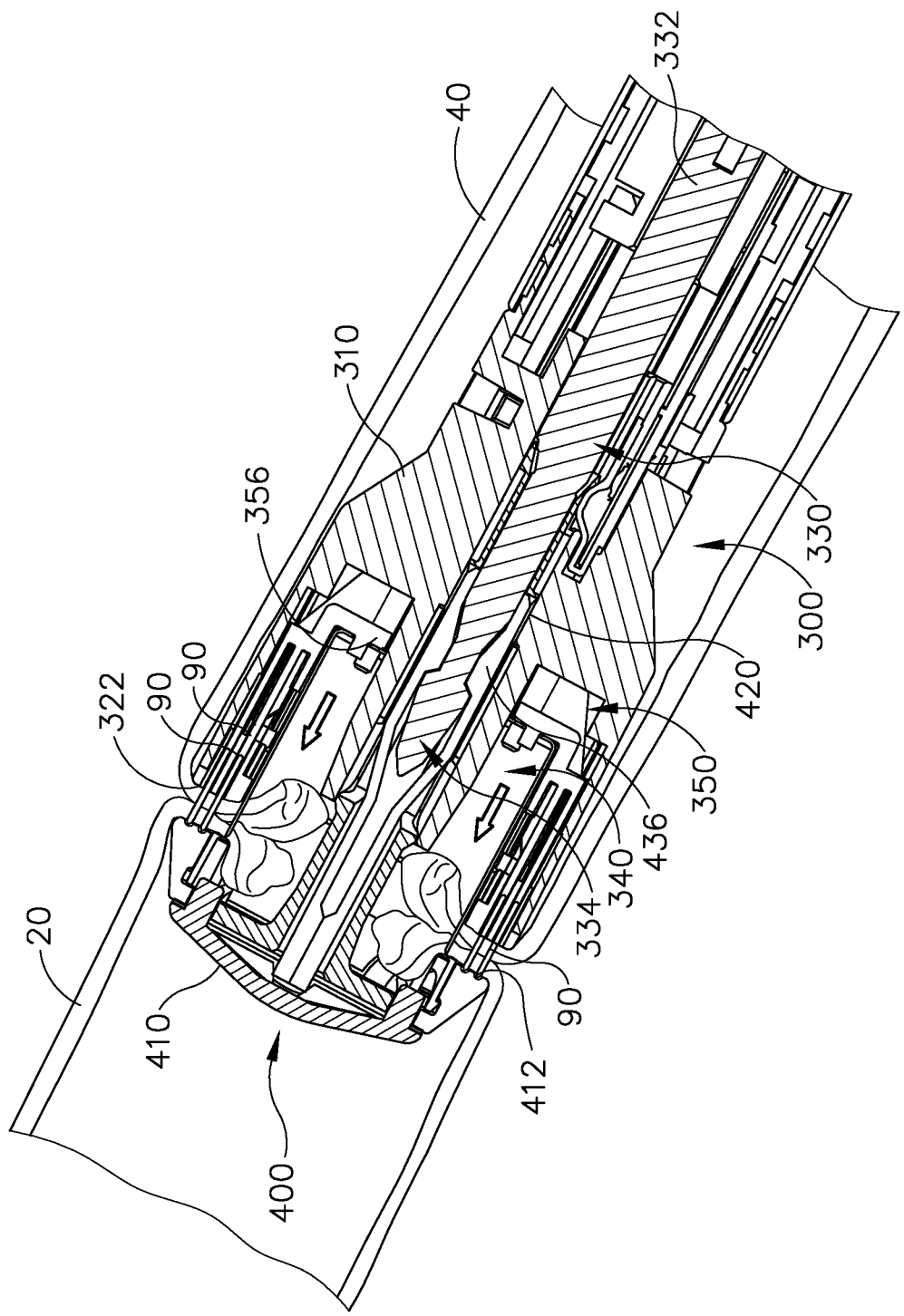
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator actuates safety trigger (140) to enable actuation of firing trigger (150). The operator then actuates firing trigger (150). This actuation of firing trigger (150) in turn actuates a switch of motor activation module (180), which in turn activates motor (160) to thereby actuate stapling head assembly (300) by driving knife member (340) and staple driver member (350) distally as shown in FIG. 7D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when knife member (340) completes a full distal range of motion from the position shown in FIG. 7C to the position shown in FIG. 7D. The drive mechanism for knife member (340) may provide an increasing mechanical advantage as knife member (340) reaches the end of its distal movement, thereby providing greater force by which to break washer (417). Of course, breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and cutting edge (342).

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together, thereby coupling tubular anatomical structure (20) with tubular anatomical structure (40).

Figure 7E:
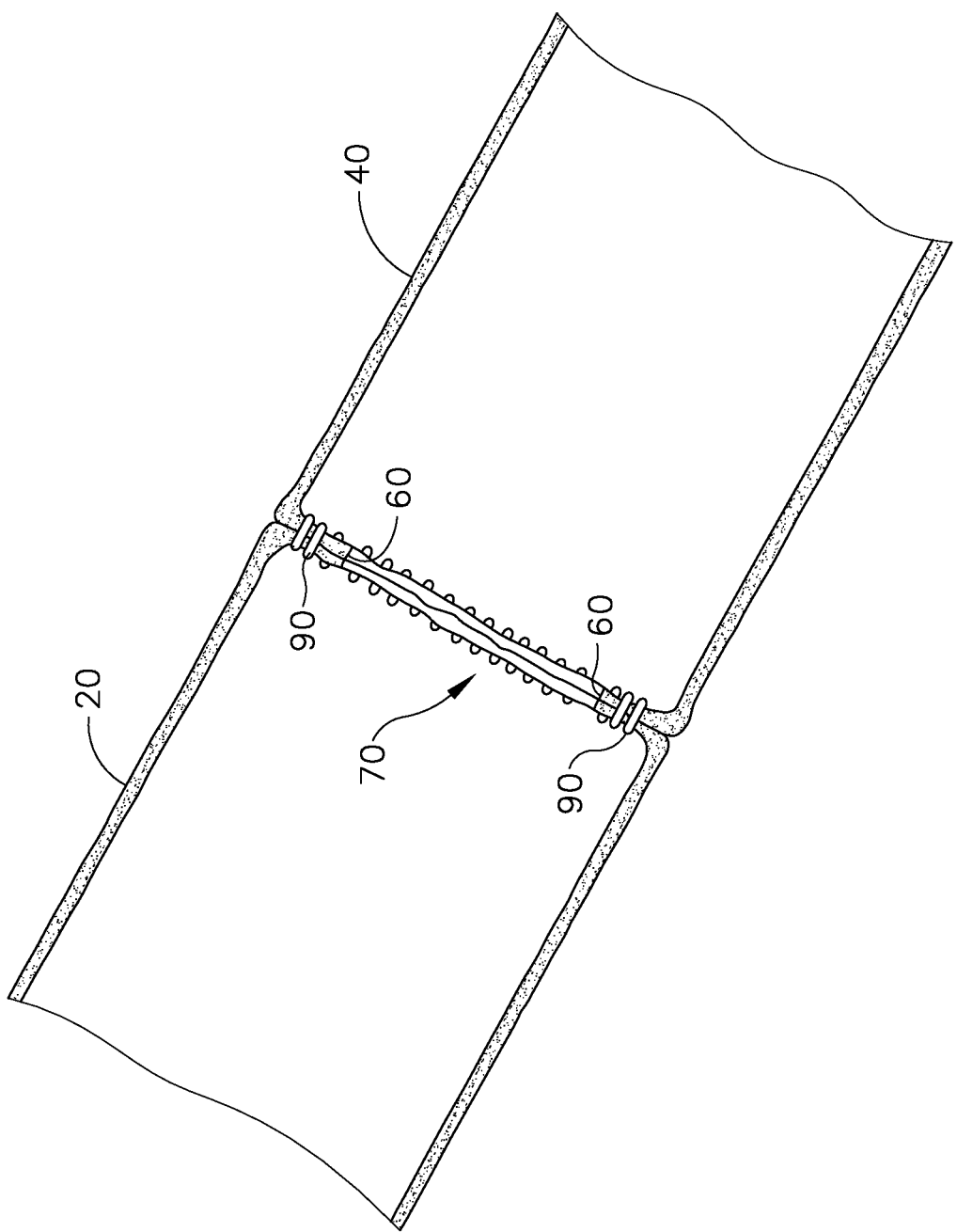
FIG. 7E depicts a cross-sectional side view of the first and second sections of the digestive tract of FIG. 7A joined together at an end-to-end anastomosis.

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. First Exemplary Alternative Deck Member for Stapling Head Assembly

Figure 8:
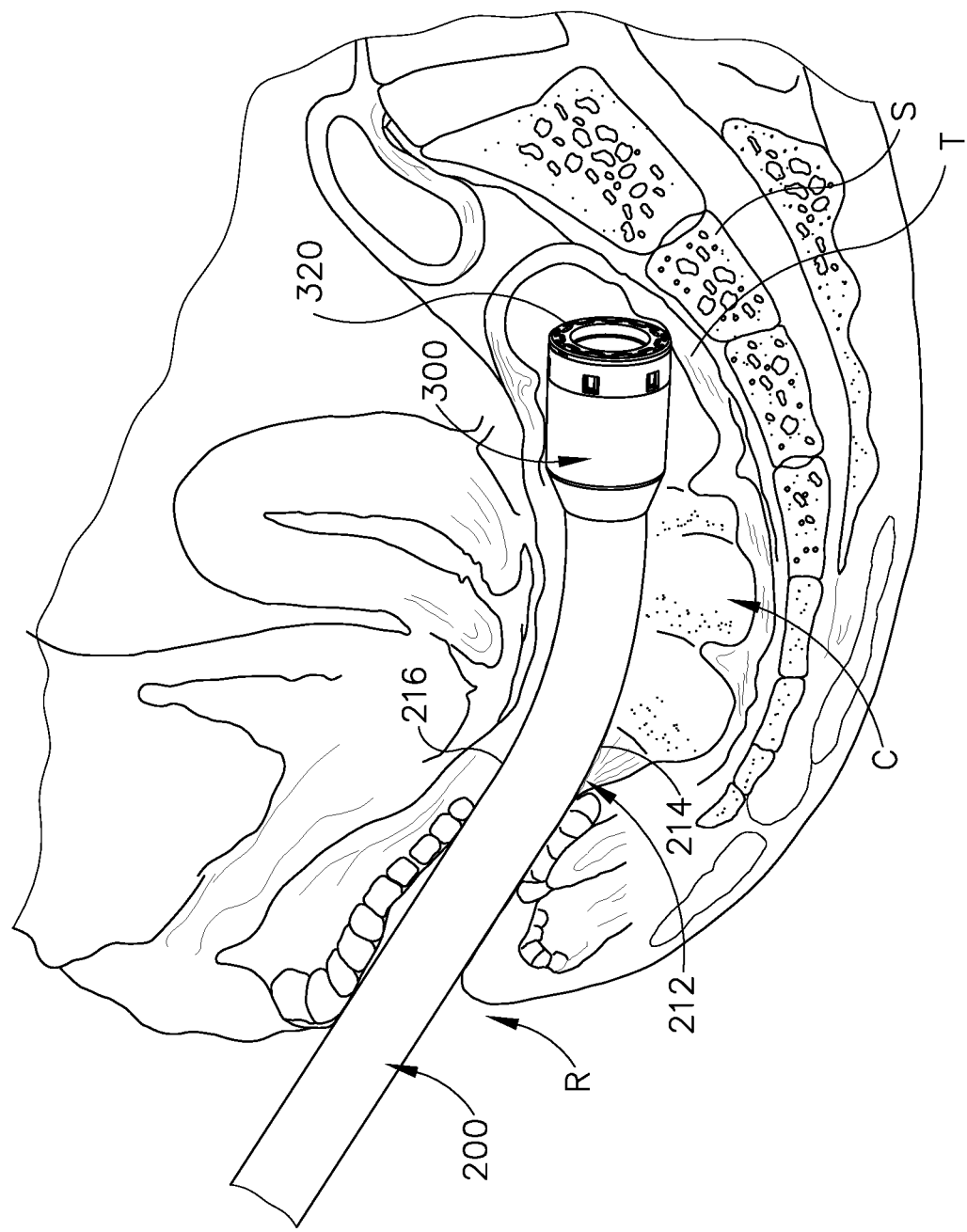
FIG. 8 depicts a partial perspective view of the stapling head assembly and shaft assembly of the circular stapler of FIG. 1 inserted in a patient's colon, with the stapling head assembly positioned near the patient's sacrum, and with the patient's anatomy shown in cross-section.

As noted above, in some instances, anatomical structures (20, 40) may comprise sections of a patient's colon. FIG. 8 shows stapling head assembly (300) and a distal portion of shaft assembly (200) disposed in a patient's colon (C). As shown, stapling head assembly (300) and shaft assembly (200) are inserted via the patient's rectum (R). As also shown, the curvature of curved section (212) is configured to generally complement the curvature of the patient's colon (C). Nevertheless, as also shown in FIG. 8, there may be instances where deck member (320) tends to compress tissue (T) of the patient's colon (C) against the patient's sacrum (S) and/or some other substantially rigid anatomical structure. Depending on the angle at which the operator has inserted stapling head assembly (300) and shaft assembly (200), and/or depending on the force that the operator is applying to stapling head assembly (300) and shaft assembly (200) during insertion, the tissue (T) of the patient's colon (C) may become damaged (e.g., torn) when the tissue (T) is pinched between stapling head assembly (300) and the patient's sacrum (S). In versions where deck member (320) has tissue gripping features and/or other protruding features (e.g., staple guidance features, etc.), such features may increase the risk of damage to the tissue (T) of the patient's colon (C) as stapling head assembly (300) and shaft assembly (200) are being inserted into the patient's colon (C).

Figure 9:
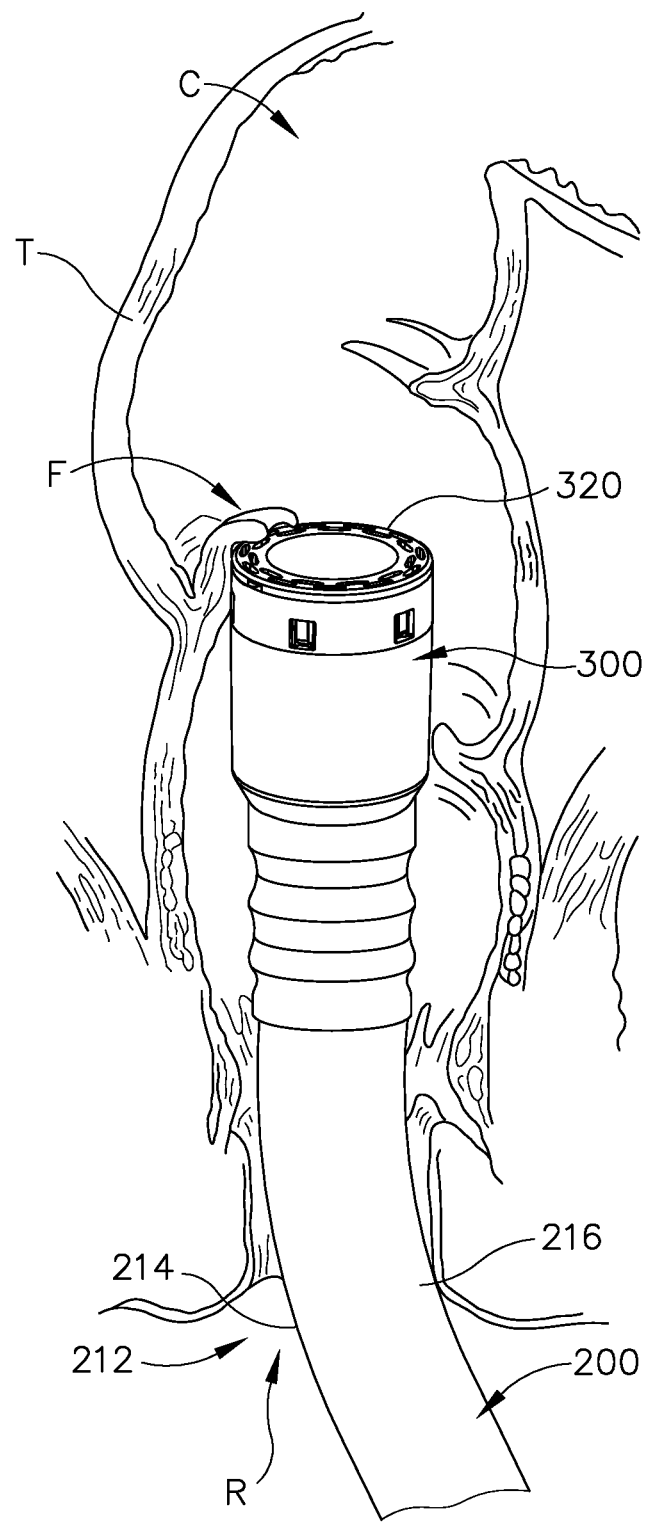
FIG. 9 depicts a partial perspective view of the stapling head assembly and shaft assembly of the circular stapler of FIG. 1 inserted in a patient's colon, with the stapling head assembly engaging a fold of the colon tissue, and with the patient's anatomy shown in cross-section.

Similarly, as shown in FIG. 9, those of ordinary skill in the art will recognize that the tissue (T) of the colon (C) defines a plurality of folds (F), and that stapling head assembly (300) may get snagged on such folds (F) as stapling head assembly (300) and shaft assembly (200) are inserted in the patient's colon (C). This snagging may also create a risk of damaging the tissue (T) of the patient's colon (C). Again, in versions where deck member (320) has tissue gripping features and/or other protruding features (e.g., staple guidance features, etc.), such features may increase the risk of damage to the tissue (T) of the patient's colon (C) as stapling head assembly (300) gets snagged on folds (F).

It may therefore be desirable to provide a version of stapling head assembly (300) that minimizes the risk of damaging the tissue (T) of the patient's colon (C) during insertion of stapling head assembly (300) and shaft assembly (200) into the patient's colon (C). Moreover, it may be desirable to provide a version of stapling head assembly (300) that includes features that enhance gripping of tissue during actuation of stapling head assembly (300), thereby promoting successful tissue cutting and staple deployment, without increasing the risk of damaging the tissue (T) of the patient's colon (C) during insertion of stapling head assembly (300) and shaft assembly (200) into the patient's colon (C).

FIGS. 10-15 show an exemplary alternative deck member (500) that may be readily incorporated into stapling head assembly (300) in place of deck member (320). Except as otherwise described below, deck member (500) of this example is substantially similar to deck member (320) described above. Deck member (500) of this example includes a deck surface (522) defining two concentric annular arrays of staple openings (524). Staple openings (524) are arranged to correspond with the arrangement of staple drivers (352) and staple forming pockets (414) described above. Thus, each staple opening (524) is configured to provide a path for a corresponding staple driver (352) to drive a corresponding staple through deck member (500) and into a corresponding staple forming pocket (414) when a stapling head assembly (300) incorporating deck member (500) is actuated. Deck member (500) defines an inner diameter that is just slightly larger than the outer diameter defined by knife member (340). Deck member (500) is thus configured to allow knife member (340) to translate distally to a point where cutting edge (342) is distal to the plane of deck surface (522).

Figure 10:
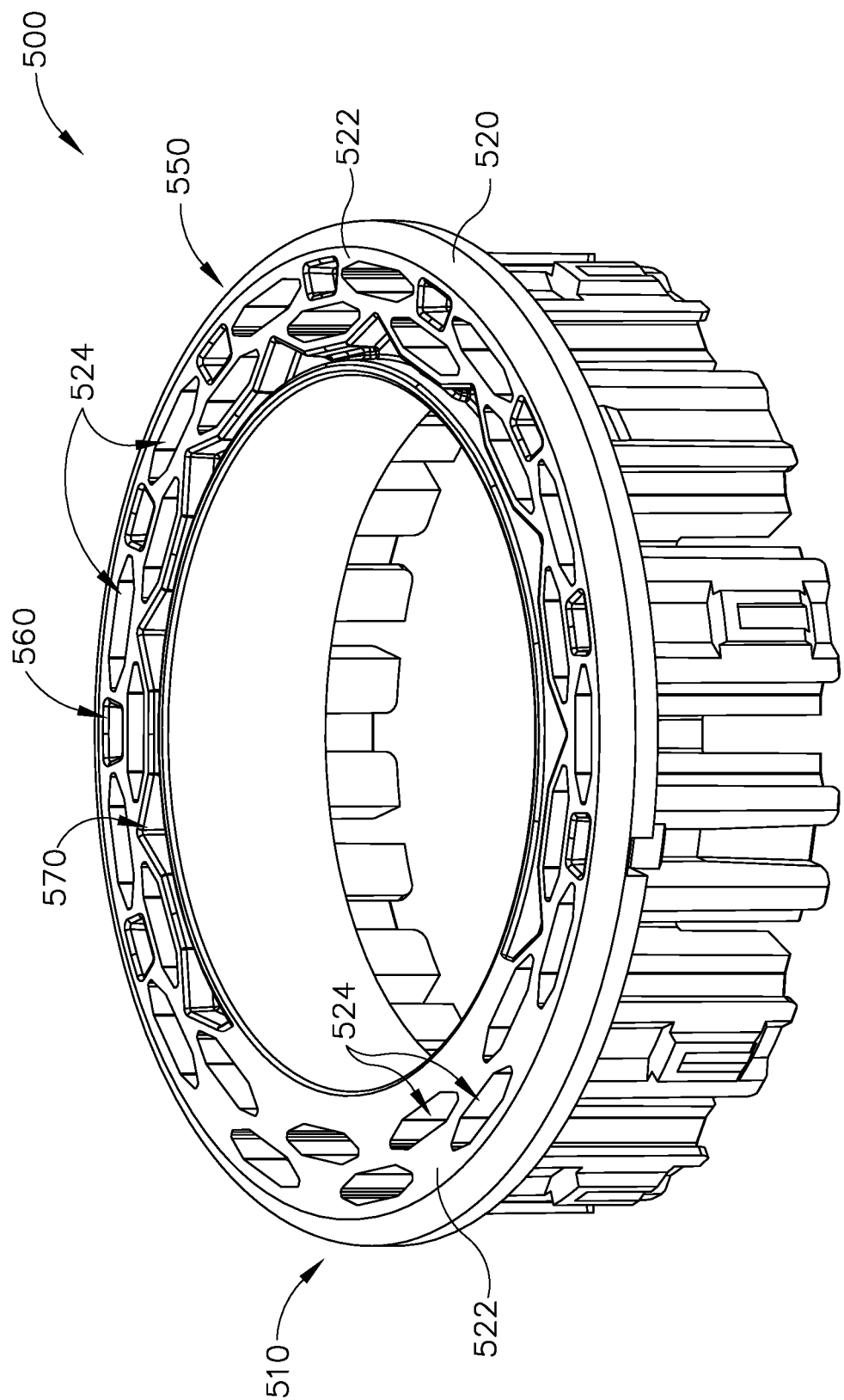
FIG. 10 depicts a perspective view of an exemplary alternative deck member that may be incorporated into the stapling head assembly of FIG. 4.
Figure 11:
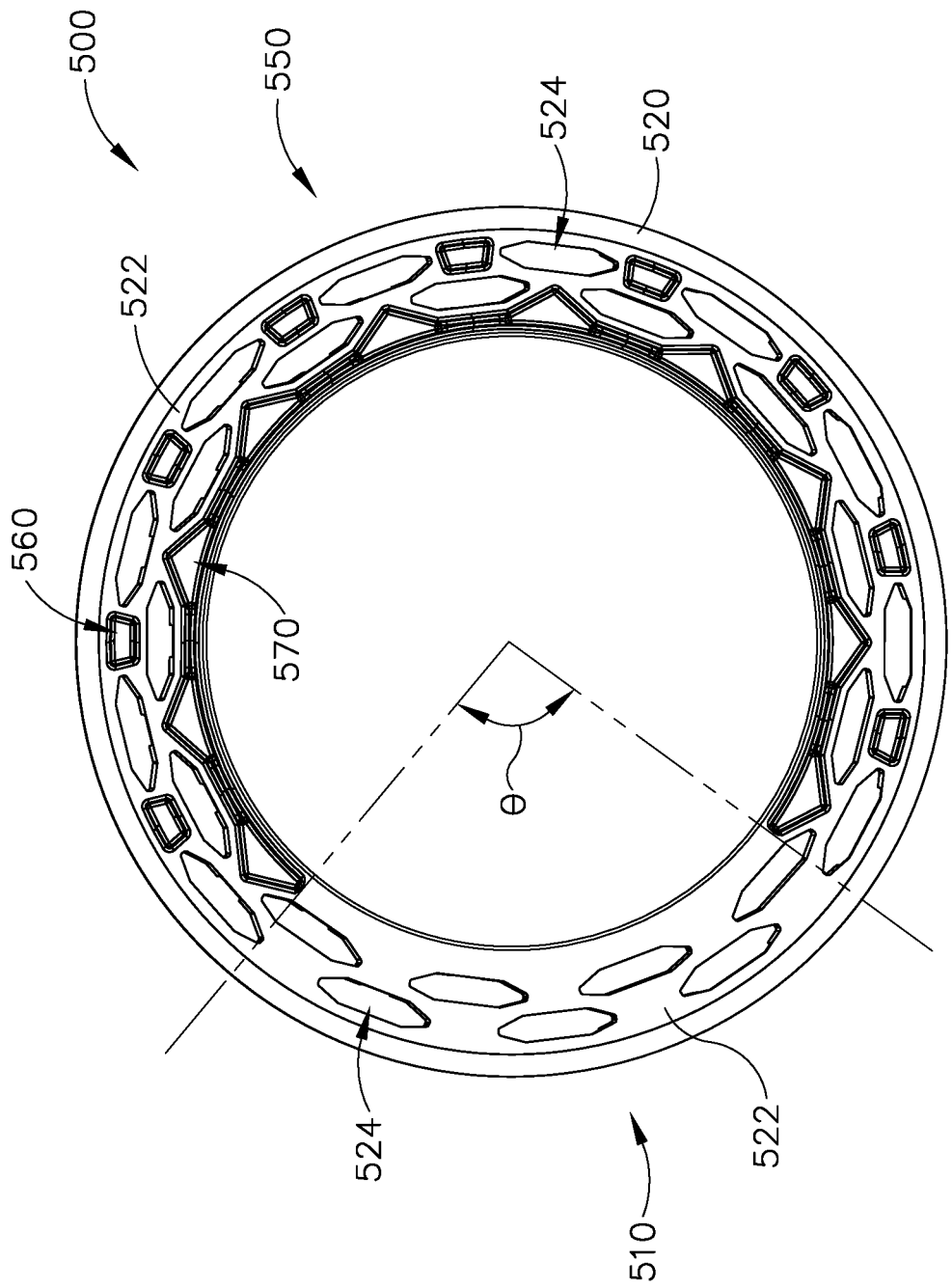
FIG. 11 depicts a top plan view of the deck member of FIG. 10.
Figure 12:
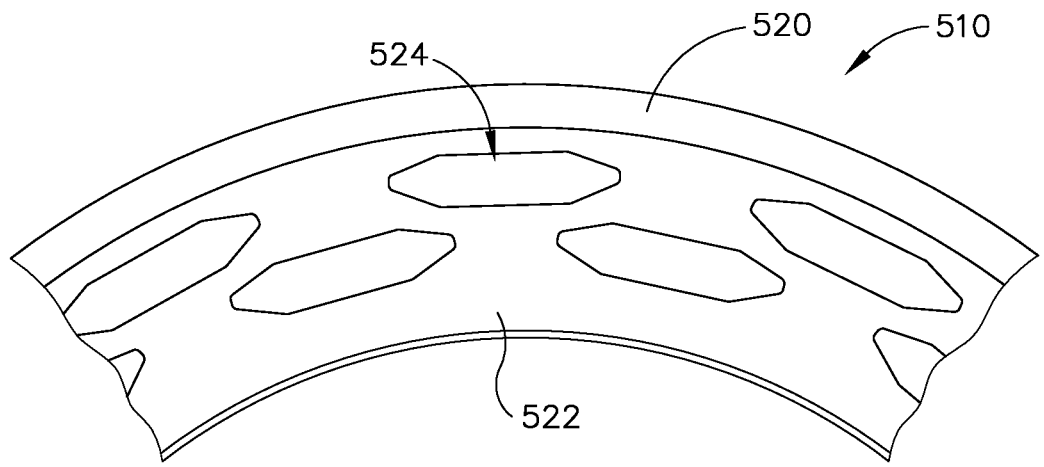
FIG. 12 depicts a partial top plan view of a first portion of the deck member of FIG. 10.

Unlike deck member (320) described above, deck member (500) of the present example includes a first zone (510) and a second zone (550). As best seen in FIGS. 10-12, first zone (510) is characterized in that deck surface (522) is substantially flat within first zone (510). By contrast, as best seen in FIGS. 10-11 and 13-15, second zone (550) is characterized in that a plurality of recesses (560, 570) are formed in deck surface (522) within second zone (550). As best seen in FIG. 11, first zone (510) spans along an angular range (θ) of approximately 90° of the circumference of deck member (500). By way of further example only, first zone (510) may span along an angular range (θ) of less than approximately 90° of the circumference of deck member (500). For instance, first zone (510) may span along an angular range (θ) between approximately 30° and approximately 90° of the circumference of deck member (500); or between approximately 45° and approximately 90° of the circumference of deck member (500).

It should be understood that providing the two different zones (510, 520) is merely optional. For instance, some variations of deck member (500) may include the features of second zone (550) about the entire circumference of deck member (500), rather than being limited to only a portion of the circumference of deck member (500) as shown in FIGS. 10-11. In other words, the angular range (θ) of first zone (510) may be 0° in some versions.

As also shown in FIGS. 10-11, outer edge (520) of deck member (500) spans around the full circumference of deck member (500) with a consistent surface geometry. In particular, and as best seen in FIGS. 14-15, outer edge (520) is curved in this example to prevent outer edge (520) from snagging on tissue (T).

Figure 13:
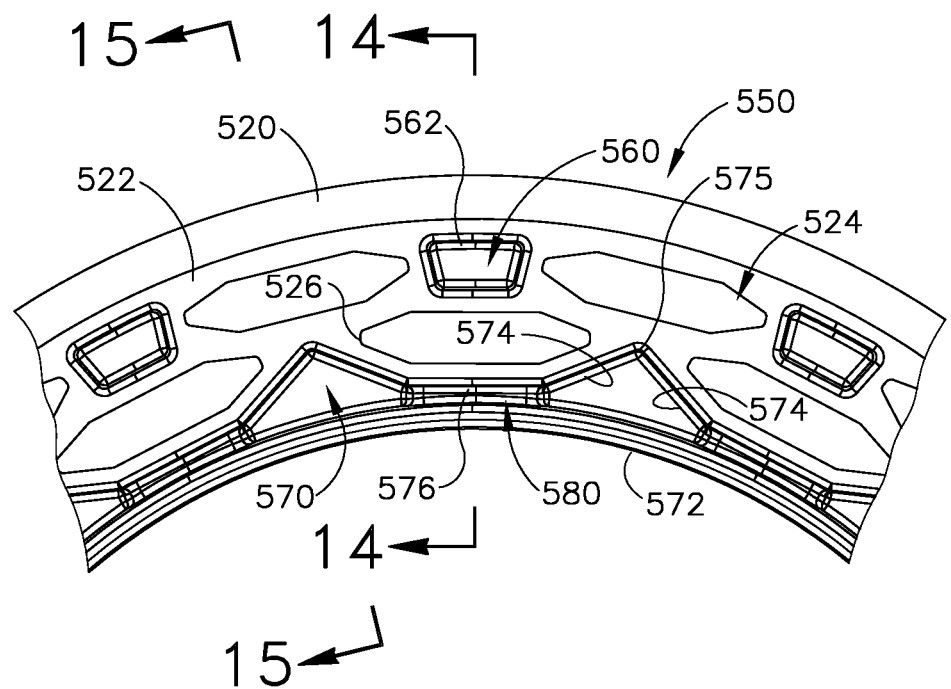
FIG. 13 depicts a partial top plan view of a second portion of the deck member of FIG. 10.
Figure 14:
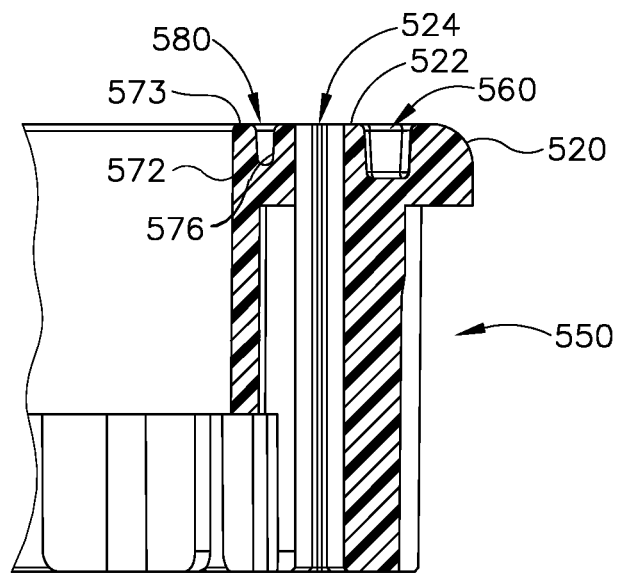
FIG. 14 depicts a cross-sectional view of the deck member of FIG. 10, taken along line 14-14 of FIG. 13.
Figure 15:
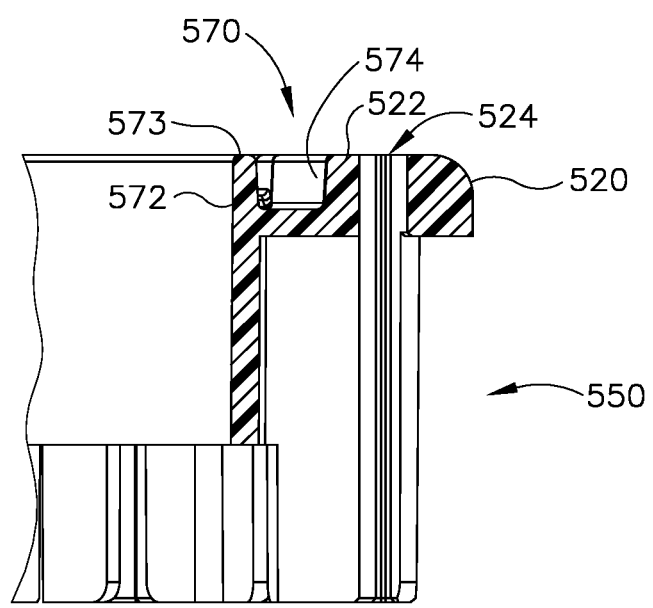
FIG. 15 depicts a cross-sectional view of the deck member of FIG. 10, taken along line 15-15 of FIG. 13.

FIGS. 13-15 show second zone (550) in further detail. In particular, FIG. 13 shows how, within second zone (550), recesses (560) are spaced between the outermost annular array of staple openings (524); while portions of recesses (570) are spaced between the staple openings (524) of the inner annular array of staple openings (524). In the present example, recesses (560) are shaped like isosceles trapezoids, with the widest sides (562) of the trapezoid shapes being positioned as the radially outermost sides of the trapezoids. It should be understood that recesses (560) may have any other suitable configuration. It should also be understood that, in the present example, the region of deck surface (522) surrounding recesses (560) is flush with the region of deck surface (522) in first zone (520).

Recesses (570) of the present example are generally shaped like isosceles triangles, with each triangle being defined by a pair of straight walls (574) having equal length and an inner annular wall (572). The vertexes (575) formed by walls (574) are positioned at the radially outermost points of recesses (570). In particular, vertexes (575) are located at radial positions corresponding to the same circumference at which angularly outermost points (526) of staple openings (524) are located. In other words, vertexes (575) and points (526) are all positioned at the same radial distance along the same circumference in this example. Alternatively, the position and configuration of recesses (570) may have any other suitable relationship with the position and configuration of staple openings (524). Recesses (570) of the present example are joined together by channels (580) which are defined between inner annular wall (572) and respective opposing annular walls (576). Walls (572, 576) are parallel with each other and are closely positioned relative to each other, such that channels (580) are substantially small in comparison to recesses (560, 570).

Recesses (560, 570) and channels (580) are configured to receive tissue as tissue is being compressed against deck surface (522) by anvil (400) as described above. In particular, when anvil (400) is actuated via knob (130) to compress tissue between anvil (400) and deck surface (522), portions of the compressed tissue will enter recesses (560, 570) and channels (580). By having some of the tissue enter recesses (560, 570) and channels (580), this may reduce the total pressure that would otherwise be applied to the tissue if the tissue were being compressed against a consistently flat deck surface like deck surface (322). By reducing the total pressure on the tissue, deck member (500) may reduce the risk of the tissue from becoming fractured by over-compression. In addition to reducing the total pressure on tissue, the entry of tissue portions in recesses (560, 570) and channels (580) may provide a grip on the compressed tissue that is greater than the grip that could otherwise be achieved using a consistently flat deck surface like deck surface (322). The enhanced grip of tissue may promote cleaner cutting by knife member (340) and also promote more successful deployment of staples (90) in the tissue. Thus, the presence of recesses (560, 570) and channels (580) may both reduce the risk of over-compression of tissue and promote greater success in cutting and stapling the tissue.

In the present example, and as best seen in FIGS. 14-15, recesses (560, 570) and channels (580) all extend to substantially the same depth within deck member (500). In some other versions, recesses (560, 570) and channels (580) extend to different depths. For instance, recesses (560) may extend to greater depths than recesses (570) or vice versa. It should also be understood that recesses (560) may alternate depths, such that the recesses (560) alternate between a relatively shallow recess (560) and a relatively deep recess (560) along at least a portion of the angular range of second zone (550). Similarly, recesses (570) may alternate depths, such that the recesses (570) alternate between a relatively shallow recess (570) and a relatively deep recess (570) along at least a portion of the angular range of second zone (550). As yet another merely illustrative variation, the depth of a given recess (560, 570) may vary within that particular recess (560, 570). For instance, the radially innermost region of a given recess (560) may be deeper or shallower than the radially outermost region of that same recess (560). Similarly, the region of each recess (570) near vertex (575) may be deeper or shallower than the region of each recess (570) near inner annular wall (572). Other suitable variations that may be provided in the depth of recesses (560, 570) and/or channels (580) will be apparent to those of ordinary skill in the art in view of the teachings herein.

Inner annular wall (572) extends consistently along the full circumference of deck member (500). In particular, the height of the uppermost edge (573) of inner annular wall (572) is consistent along the full circumference of deck member (500). Uppermost edge (573) is thus configured to provide consistent pressure against the adjacent annular region of tissue as the tissue is being compressed against deck member (500) by anvil (400). This application of consistent pressure against the adjacent annular region of tissue may further assist in clean cutting of the tissue by knife member (340), particularly since knife member (340) will be severing the tissue right next to uppermost edge (573). As best seen in FIGS. 14-15, uppermost edge (573) of inner annular wall (572) is substantially flush with deck surface (522) in the present example. In some other variations, uppermost edge (573) is proud or raised relative to deck surface (522).

As noted above, the entry of tissue into recesses (560, 570) and channels (580) may reduce the risk of over-compression of tissue and promote greater success in cutting and stapling the tissue during actuation of anvil (400) and stapling head assembly (300). However, this same entry of tissue in into recesses (560, 570) and channels (580) may present some risks during insertion of stapling head assembly (300) and shaft assembly (200) into tissue. In other words, in variations of deck member (500) where recesses (560, 570) are positioned along the full circumference of deck member (500), there may be a tendency for tissue (T) to enter recesses (560, 570) and channels (580) during insertion of shaft assembly (200) and a stapling head assembly (300) incorporating the variation of deck member (500) into the patient's colon (C). Such entry of tissue into recesses (560, 570) and channels (580) may increase the risk of damage to tissue (T) in the event that the tissue (T) is being pinched against the sacrum (S) as described above with reference to FIG. 8.

To avoid the above-noted risks that might otherwise be associated with tissue entering recesses (560, 570) and channels (580) during insertion of shaft assembly (200) and stapling head assembly (300) incorporating deck member (500) into the patient's colon (C), first zone (510) is positioned to correspond with outer curve (214) of curved section (212) of shaft assembly (200). As shown in FIG. 8, the region of stapling head assembly (300) corresponding to outer curve (214) is the region of stapling head assembly (300) that would tend to pinch the tissue (T) against the sacrum (S). Thus, by having first zone (510) in this region, deck member (500) avoids the risks that might otherwise be associated with recesses (560, 570) and channels (580) during insertion of shaft assembly (200) and stapling head assembly (300) incorporating deck member (500) into the patient's colon (C); while still providing the advantages of having recesses (560, 570) and channels (580) in second zone when anvil (400) and stapling head assembly (300) are actuated.

III. Exemplary Alternative Deck Member for Stapling Head Assembly

Figure 16:
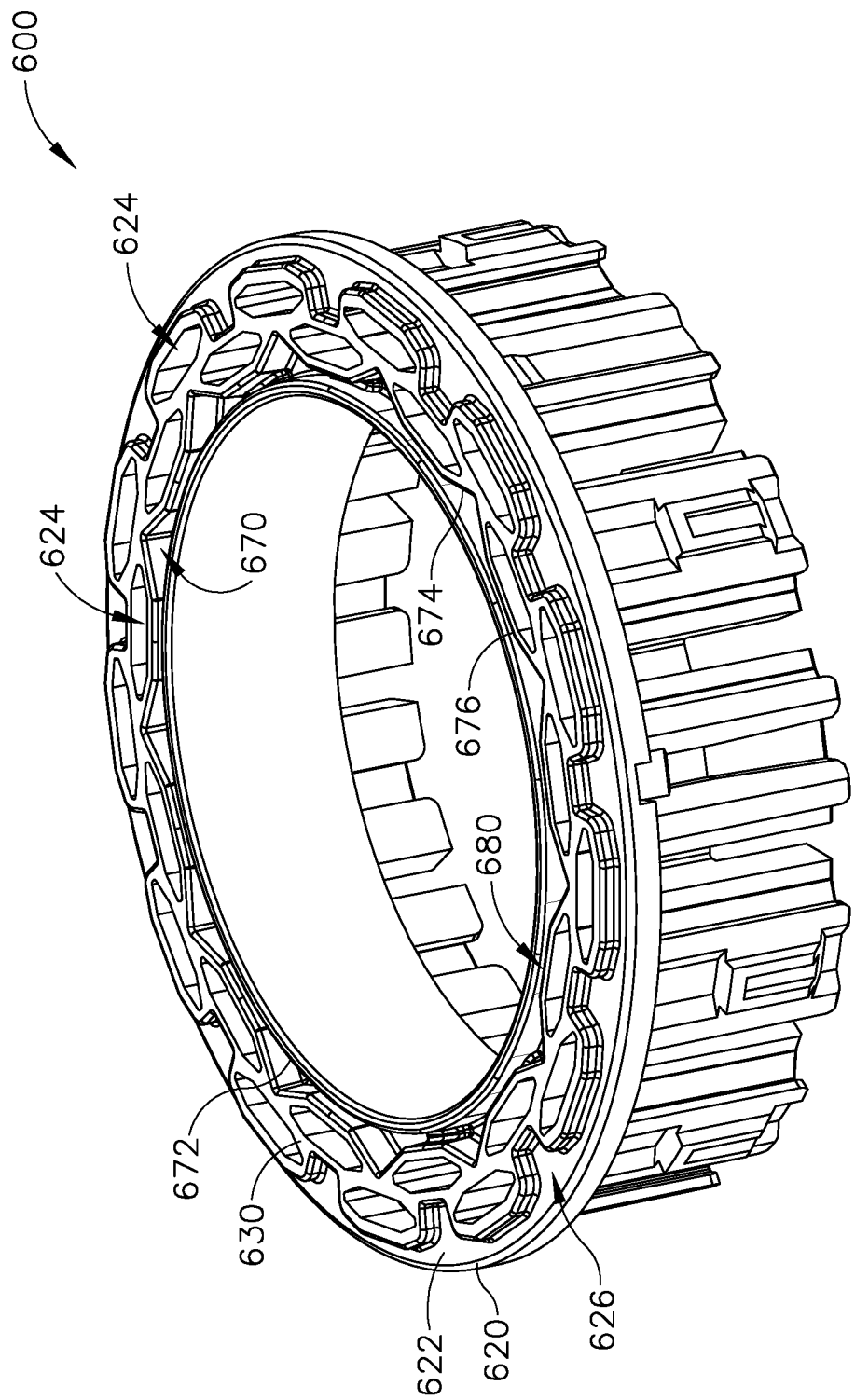
FIG. 16 depicts a perspective view of another exemplary alternative deck member that may be incorporated into the stapling head assembly of FIG. 4.
Figure 17:
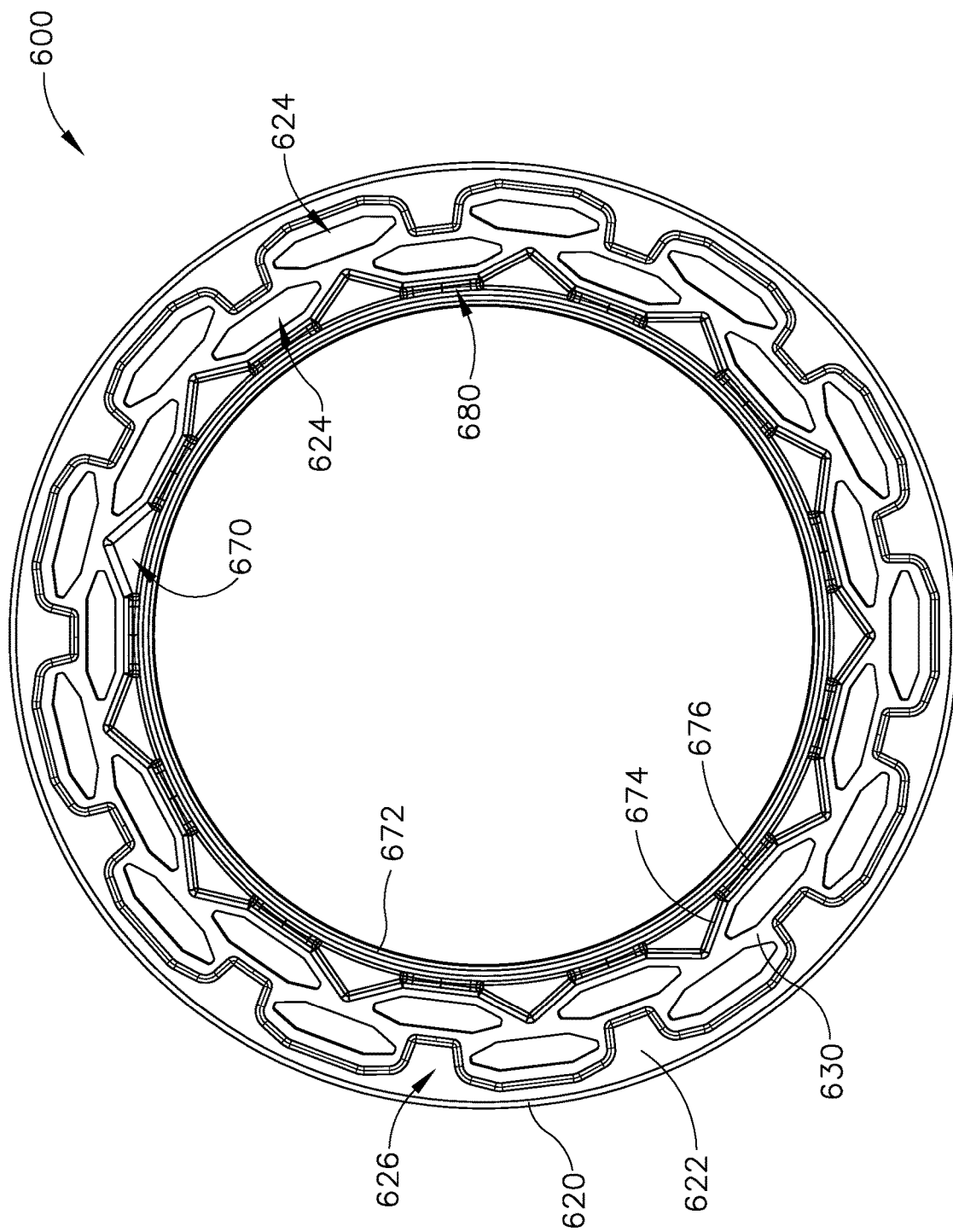
FIG. 17 depicts a top plan view of the deck member of FIG. 16.

FIGS. 16-17 show another exemplary alternative deck member (600) that may be readily incorporated into stapling head assembly (300) in place of deck member (320). Except as otherwise described below, deck member (600) of this example is substantially similar to deck member (500)

described above. Deck member (600) of this example includes a first deck surface (622), a second deck surface (630), and two concentric annular arrays of staple openings (624). Staple openings (624) are arranged to correspond with the arrangement of staple drivers (352) and staple forming pockets (414) described above. Thus, each staple opening (624) is configured to provide a path for a corresponding staple driver (352) to drive a corresponding staple through deck member (600) and into a corresponding staple forming pocket (414) when a stapling head assembly (300) incorporating deck member (600) is actuated. Deck member (600) defines an inner diameter that is just slightly larger than the outer diameter defined by knife member (340). Deck member (600) is thus configured to allow knife member (340) to translate distally to a point where cutting edge (342) is distal to the plane of second deck surface (630).

Unlike deck member (500) described above, deck member (600) of the present example does not include different zones providing different structures based on the angular position about an axis passing through the center of deck member (600). Thus, the structure of deck member (600) is consistent along the full circumference of deck member.

In the present example, an outer edge (620) spans around the full circumference of deck member (500) with a consistent surface geometry. In the present example, outer edge (620) is configured to prevent outer edge (520) from snagging on tissue (T). In some versions, outer edge (620) has a curved profile. In some other versions, outer edge (620) has a chamfered profile. Alternatively, outer edge (620) may have any other suitable kind of profile.

Second deck surface (630) is proud relative to first deck surface (620), such that first deck surface (620) is recessed relative to second deck surface (630). As shown, second deck surface (630) fully surrounds each and every staple opening (624), including the inner array of staple openings (624) and the outer array of staple openings (624). However, first deck surface (620) extends inwardly between staple openings (624) of the outer array of staple openings (624), thereby creating gaps (626) in second deck surface (630) between staple openings (624) of the outer array of staple openings (624).

A plurality of recesses (670) are spaced between the staple openings (624) of the inner annular array of staple openings (624). Recesses (670) of this example are identical to recesses (570) described above. In particular, recesses (670) of the present example are generally shaped like isosceles triangles, with each triangle being defined by a pair of straight walls (674) having equal length and an inner annular wall (672). The vertexes formed by walls (674) are positioned at the radially outermost points of recesses (670). In particular, these vertexes are located at radial positions corresponding to the same circumference at which the angularly outermost points of staple openings (624) are located. In other words, these vertexes of recesses (670) and corresponding points of staple openings (624) are all positioned at the same radial distance along the same circumference in this example. Alternatively, the position and configuration of recesses (670) may have any other suitable relationship with the position and configuration of staple openings (624).

Recesses (670) of the present example are joined together by channels (680) which are defined between inner annular wall (672) and respective opposing annular walls (676). Walls (672, 676) are parallel with each other and are closely positioned relative to each other, such that channels (680) are substantially small in comparison to recesses (670).

Gaps (626), recesses (670), and channels (680) are configured to receive tissue as tissue is being compressed against deck surfaces (622, 630) by anvil (400) as described above. In particular, when anvil (400) is actuated via knob (130) to compress tissue between anvil (400) and deck surfaces (622, 630), portions of the compressed tissue will enter gaps (626), recesses (670), and channels (680). By having some of the tissue enter gaps (626), recesses (670), and channels (680), this may reduce the total pressure that would otherwise be applied to the tissue if the tissue were being compressed against a consistently flat deck surface like deck surface (322). By reducing the total pressure on the tissue, deck member (600) may reduce the risk of the tissue from becoming fractured by over-compression. In addition to reducing the total pressure on tissue, the entry of tissue portions in gaps (626), recesses (670), and channels (680) may provide a grip on the compressed tissue that is greater than the grip that could otherwise be achieved using a consistently flat deck surface like deck surface (322). The enhanced grip of tissue may promote cleaner cutting by knife member (340) and also promote more successful deployment of staples (90) in the tissue. Thus, the presence of gaps (626), recesses (670), and channels (680) may both reduce the risk of over-compression of tissue and promote greater success in cutting and stapling the tissue.

In the present example, and as best seen in FIGS. 14-15, gaps (626), recesses (670), and channels (680) all extend to substantially the same depth relative to second deck surface (630). In some other versions, gaps (626), recesses (670), and channels (680) extend to different depths relative to second deck surface (630). For instance, gaps (626) may extend to greater depths than recesses (670) relative to second deck surface (630) or vice versa. It should also be understood that gaps (626) may alternate depths relative to second deck surface (630), such that gaps (626) alternate between a relatively shallow gap (626) and a relatively deep gap (626) along at least a portion of the angular range of deck member (600). Similarly, recesses (670) may alternate depths relative to second deck surface (630), such that recesses (670) alternate between a relatively shallow recess (670) and a relatively deep recess (670) along at least a portion of the angular range of deck member (600). As yet another merely illustrative variation, the depth of a given gap (626) or recess (670) may vary within that particular gap (626) or recess (670). For instance, the radially innermost region of a given gap (626) may be deeper or shallower than the radially outermost region of that same gap (626). Similarly, the region of each recess (670) near the vertex may be deeper or shallower than the region of each recess (670) near inner annular wall (672). Other suitable variations that may be provided in the depth of gaps (626), recesses (670), and/or channels (680) relative to second deck surface (630) will be apparent to those of ordinary skill in the art in view of the teachings herein.

Inner annular wall (672) extends consistently along the full circumference of deck member (600). In particular, the height of the uppermost edge of inner annular wall (672) is consistent along the full circumference of deck member (500). The uppermost edge of inner annular wall (672) is thus configured to provide consistent pressure against the adjacent annular region of tissue as the tissue is being compressed against deck member (600) by anvil (400). This application of consistent pressure against the adjacent annular region of tissue may further assist in clean cutting of the tissue by knife member (340), particularly since knife member (340) will be severing the tissue right next to the uppermost edge of inner annular wall (672). In the present example, the uppermost edge of inner annular wall (672) is substantially flush with second deck surface (630). In some other variations, the uppermost edge of inner annular wall (672) is proud or raised relative to second deck surface (630).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly has a distal end; (c) a stapling head assembly located at the distal end of the shaft assembly, wherein the stapling head assembly comprises: (i) a deck member, wherein the deck member comprises: (A) a deck surface, (B) an outer annular array of staple openings formed through the deck surface, (C) an inner annular array of staple openings formed through the deck surface, and (D) a plurality of recesses formed in the deck surface, wherein at least a portion of the recesses are positioned between at least some of the staple openings, (ii) a plurality of staples, and (iii) a driver operable to drive the staples through the staple openings; and (d) an anvil, wherein the anvil is operable to compress tissue against the deck surface.

Example 2

The apparatus of Example 1, wherein the plurality of recesses comprises a first plurality of recesses and a second plurality of recesses, wherein at least a portion of the recesses of the first plurality of recesses are positioned between the staple openings of the outer annular array of staple openings, wherein at least a portion of the recesses of the second plurality of recesses are positioned between the staple openings of the inner annular array of staple openings.

Example 3

The apparatus of any one or more of Examples 1 through 2, wherein the plurality of recesses comprises an outer plurality of recesses, wherein the recesses of the outer plurality of recesses are positioned between the staple openings of the outer annular array of staple openings.

Example 4

The apparatus of Example 3, wherein the recesses of the outer plurality of recesses are formed discretely relative to each other such that the recesses of the outer plurality of recesses are isolated relative to each other.

Example 5

The apparatus of Example 3, wherein at least some of the recesses of the outer plurality of recesses have a trapezoidal shape.

Example 6

The apparatus of any one or more of Examples 1 through 5, wherein the plurality of recesses comprises an inner plurality of recesses, wherein the recesses of the inner plurality of recesses are positioned between the staple openings of the inner annular array of staple openings.

Example 7

The apparatus of Example 6, wherein the recesses of the inner plurality of recesses are in communication with each other via channels.

Example 8

The apparatus of any one or more of Examples 6 through 7, wherein at least some of the recesses of the outer plurality of recesses have a triangular shape.

Example 9

The apparatus of Example 8, wherein the triangular shape is defined in part by a pair of corresponding sidewalls joined at a vertex, wherein the vertex is located at a radial position on a circumference corresponding to radial positions of ends of the staple openings of the inner annular array of staple openings.

Example 10

The apparatus of any one or more of Examples 1 through 9, wherein the deck member defines a first angular region along the deck surface, wherein the deck member further defines a second angular region along the deck surface, wherein the staple openings extend along the first and second angular regions, wherein the plurality of recesses extend along the second angular region, wherein the plurality of recesses do not extend along the first angular region.

Example 11

The apparatus of Example 10, wherein the first angular region extends along an angular range between approximately 30° and approximately 90° of a circumference of the deck member.

Example 12

The apparatus of any one or more of Examples 10 through 11, wherein the shaft assembly comprises a curved section including an inner curve and an outer curve.

Example 13

The apparatus of Example 12, wherein the first angular region is angularly positioned to correspond with the outer curve, wherein the second angular region is angularly positioned to correspond with the inner curve.

Example 14

The apparatus of any one or more of Examples 1 through 13, wherein the deck member further comprises a rounded outer edge.

Example 15

The apparatus of any one or more of Examples 1 through 14, wherein the deck member further comprises an inner annular wall having an uppermost edge, wherein the uppermost edge has a uniform height along a full circumference of the deck member.

Example 16

The apparatus of Example 15, wherein the uppermost edge is level with the deck surface.

Example 17

An apparatus comprising a stapling head assembly, wherein the stapling head assembly comprises: (a) an annular deck member, wherein the annular deck member comprises: (i) a deck surface, (ii) an outer annular array of staple openings formed through the deck surface, (iii) an outer plurality of recesses formed in the deck surface, wherein at least a portion of the recesses of the outer plurality of recesses are positioned between at least some of the staple openings of the outer annular array of staple openings, (iv) an inner annular array of staple openings formed through the deck surface, and (v) an inner plurality of recesses formed in the deck surface, wherein at least a portion of the recesses of the inner plurality of recesses are positioned between at least some of the staple openings of the inner annular array of staple openings; (b) a plurality of staples; and (c) a driver operable to drive the staples through the staple openings.

Example 18

The apparatus of Example 17, wherein the deck member defines a first angular region along the deck surface, wherein the deck member further defines a second angular region along the deck surface, wherein the first and second angular regions together extend along a full circumference of the deck member, wherein the inner and outer annular arrays of staple openings extend along the first and second angular regions, wherein the inner and outer pluralities of recesses are absent from the first angular region.

Example 19

The apparatus of any one or more of Examples 17 through 18, wherein the recesses of the inner plurality of recesses have a same depth as the recesses of the outer plurality of recesses.

Example 20

An apparatus comprising: (a) a shaft assembly extending distally from the body, wherein the shaft assembly comprises: (i) a proximal end, (ii) a distal end, and (iii) a curved section located between the proximal end and the distal end, wherein the curved section includes an inner curve and an outer curve; and (b) a stapling head assembly located at the distal end of the shaft assembly, wherein the stapling head assembly comprises: (i) an annular deck surface defining a first angular region and a second angular region, wherein the first angular region is positioned to correspond with the outer curve of the shaft assembly, wherein the second angular region is positioned to correspond with the inner curve of the shaft assembly, (ii) an outer annular array of staple openings formed through the deck surface along the first and second angular regions, (iii) an inner annular array of staple openings formed through the deck surface along the first and second angular regions, (iv) a plurality of recesses formed in the deck surface, wherein the recesses are located in the second angular region but not in the first angular region, (v) a plurality of staples, and (vi) a driver operable to drive the staples through the staple openings.

V. Miscellaneous

It should also be understood that the teachings above may be readily combined with the teachings of U.S. patent application Ser. No. 15/350,593, entitled "Atraumatic Stapling Head Features for Circular Surgical Stapler," filed on Nov. 14, 2016, issued as U.S. Pat. No. 10,542,981 on Jan. 28, 2020, the disclosure of which is incorporated by reference herein. Various suitable ways in which the teachings herein and the teachings of U.S. patent application Ser. No. 15/350,593, issued as U.S. Pat. No. 10,542,981 on Jan. 28, 2020, may be combined will be apparent to those of ordinary skill in the art.

It should also be understood that the teachings above may be readily combined with the teachings of U.S. patent application Ser. No. 15/350,621, entitled "Staple Pocket Configurations for Circular Surgical Stapler," filed on Nov. 14, 2016, published as U.S. Pub. No. 2018/0132849 on Mar. 17, 2018, the disclosure of which is incorporated by reference herein. Various suitable ways in which the teachings herein and the teachings of U.S. patent application Ser. No. 15/350,621, Published as U.S. Pub. No. 2018/0132849 on Mar. 17, 2018, may be combined will be apparent to those of ordinary skill in the art.

It should also be understood that the teachings above may be readily combined with the teachings of U.S. patent application Ser. No. 15/350,624, entitled "Circular Surgical Stapler with Angularly Asymmetric Deck Features," filed on Nov. 14, 2016, issued as U.S. Pat. No. 10,603,041 on Mar. 31, 2020, the disclosure of which is incorporated by reference herein. Various suitable ways in which the teachings herein and the teachings of U.S. patent application Ser. No. 15/350,624, issued as U.S. Pat. No. 10,603,041 on Mar. 31, 2020, may be combined will be apparent to those of ordinary skill in the art.

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep.

14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,523,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) a body;
(b) a shaft assembly extending distally from the body, wherein the shaft assembly has a distal end;
(c) a stapling head assembly located at the distal end of the shaft assembly, wherein the stapling head assembly comprises:
(i) a deck member, wherein the deck member comprises:
(A) a deck surface,
(B) an outer annular array of staple openings formed through the deck surface,
(C) an inner annular array of staple openings formed through the deck surface, and
(D) a plurality of recesses formed in the deck surface, wherein at least a portion of each recess is positioned circumferentially between an adjacent pair of staple openings of the outer annular array or the inner annular array, wherein each recess includes a closed proximal end at a fixed depth defined by a portion of the deck member, wherein each recess is closed relative to at least one of an inner diameter or an outer diameter of the deck member,
wherein the plurality of recesses comprises an inner plurality of recesses positioned between the staple openings of the inner annular array of staple openings, wherein at least some of the recesses of the inner plurality of recesses communicate with one another via at least one channel,
(ii) a plurality of staples disposed within the staple openings of the outer and inner annular arrays, and
(iii) a driver operable to drive the staples through the staple openings of the outer and inner annular arrays; and
(d) an anvil, wherein the anvil is operable to compress tissue against the deck surface,
wherein the recesses are configured to receive and thereby grip tissue while the staples are driven distally from the staple openings through the tissue and against the anvil.

2. The apparatus of claim 1, wherein the plurality of recesses comprises a first plurality of recesses and a second plurality of recesses, wherein at least a portion of the recesses of the first plurality of recesses are positioned between the staple openings of the outer annular array of staple openings, wherein at least a portion of the recesses of the second plurality of recesses are positioned between the staple openings of the inner annular array of staple openings.

3. The apparatus of claim 1, wherein the plurality of recesses further comprises an outer plurality of recesses, wherein the recesses of the outer plurality of recesses are positioned between the staple openings of the outer annular array of staple openings.

4. The apparatus of claim 3, wherein the recesses of the outer plurality of recesses are formed discretely relative to each other such that the recesses of the outer plurality of recesses are isolated relative to each other.

5. The apparatus of claim 3, wherein at least some of the recesses of the outer plurality of recesses have a trapezoidal shape.

6. The apparatus of claim 1, wherein the at least one channel comprises a plurality of channels, wherein each of the channels interconnects a respective pair of the inner plurality of recesses.

7. The apparatus of claim 1, wherein at least some of the recesses of the inner plurality of recesses have a triangular shape.

8. The apparatus of claim 7, wherein the triangular shape is defined in part by a pair of corresponding sidewalls joined at a vertex, wherein the vertex is located at a radial position on a circumference corresponding to radial positions of ends of the staple openings of the inner annular array of staple openings.

9. The apparatus of claim 1, wherein the deck member defines a first angular region along the deck surface, wherein the deck member further defines a second angular region along the deck surface, wherein the staple openings extend along the first and second angular regions, wherein the plurality of recesses extend along the second angular region, wherein the plurality of recesses do not extend along the first angular region.

10. The apparatus of claim 9, wherein the first angular region extends along an angular range between approximately 30° and approximately 90° of a circumference of the deck member.

11. The apparatus of claim 9, wherein the shaft assembly comprises a curved section including an inner curve and an outer curve.

12. The apparatus of claim 11, wherein the first angular region is angularly positioned to correspond with the outer curve, wherein the second angular region is angularly positioned to correspond with the inner curve.

13. The apparatus of claim 1, wherein the deck member further comprises a rounded outer edge.

14. The apparatus of claim 1, wherein the deck member further comprises an inner annular wall having an uppermost edge, wherein the uppermost edge has a uniform height along a full circumference of the deck member, wherein the uppermost edge is level with the deck surface.

15. The apparatus of claim 1, wherein each recess is closed in a radial direction to at least one of the inner diameter or the outer diameter of the deck member.

16. An apparatus comprising a stapling head assembly, wherein the stapling head assembly comprises:
(a) an annular deck member, wherein the annular deck member comprises:
(i) a deck surface,
(ii) an outer annular array of staple openings formed through the deck surface,
(iii) a plurality of outer recesses formed in the deck surface, wherein each outer recess has a closed proximal end at a first fixed depth defined by a portion of the annular deck member, wherein at least a portion of each outer recess is positioned circumferentially between an adjacent pair of staple openings of the outer annular array, wherein each outer recess is closed relative to an outer diameter of the annular deck member,
(iv) an inner annular array of staple openings formed through the deck surface, and
(v) a plurality of inner recesses formed in the deck surface, wherein each inner recess has a closed proximal end at a second fixed depth defined by a portion of the annular deck member, wherein at least a portion of each inner recess is positioned circumferentially between an adjacent pair of staple openings of the inner annular array, wherein each inner recess is closed relative to an inner diameter of the annular deck member, wherein the first and second fixed depths are equal;
(b) a plurality of staples disposed within the staple openings of the outer and inner annular arrays; and
(c) a driver operable to drive the staples through the staple openings of the outer and inner annular arrays,
wherein the outer and inner recesses are configured to receive and thereby grip tissue while the staples are driven from the staple openings into the tissue.

17. The apparatus of claim 16, wherein the deck member defines a first angular region along the deck surface, wherein the deck member further defines a second angular region along the deck surface, wherein the first and second angular regions together extend along a full circumference of the deck member, wherein the inner and outer annular arrays of staple openings extend along the first and second angular regions, wherein the inner and outer recesses are absent from the first angular region.

18. An apparatus comprising:
(a) a handle assembly;
(b) a shaft assembly extending distally from the handle assembly, wherein the shaft assembly comprises:
(i) a proximal end coupled directly to the handle assembly and defining a proximal central shaft axis,
(ii) a distal end defining a distal central shaft axis that is offset from the proximal central shaft axis, and
(iii) a curved shaft section located between the proximal end and the distal end, wherein the curved shaft section extends along a curved path that curves away from the proximal central shaft axis in a direction toward the distal central shaft axis, wherein the curved shaft section includes an outer surface that defines an inner curve and an outer curve that are diametrically opposed from one another and which extend distally toward the distal end; and (c) a stapling head assembly located at the distal end of the shaft assembly, wherein the stapling head assembly comprises:
  (i) an annular deck member having a deck surface defining a first angular region and a distinct second angular region that extend circumferentially about the annular deck member, wherein the first angular region is positioned to align circumferentially with the outer curve and not the inner curve of the shaft assembly, wherein the second angular region is positioned to align circumferentially with the inner curve and not the outer curve of the shaft assembly,
  (ii) an outer annular array of staple openings formed through the deck surface along the first and second angular regions,
  (iii) an inner annular array of staple openings formed through the deck surface along the first and second angular regions,
  (iv) a plurality of recesses formed in the deck surface, wherein the recesses are located in the second angular region but not in the first angular region, wherein each recess has a closed proximal end at a fixed depth, wherein each recess is closed in a radial direction relative to an outer diameter of the annular deck member,
  (v) a plurality of staples disposed within the staple openings of the outer and inner annular arrays, and
  (vi) a driver operable to drive the staples through the staple openings of the outer and inner annular arrays,
  wherein the recesses are configured to receive and thereby grip tissue while the staples are driven from the staple openings into the tissue.

19. The apparatus of claim 18, wherein each recess is closed in a radial direction relative to an inner diameter of the annular deck member.

20. The apparatus of claim 18, wherein the plurality of recesses comprises an inner plurality of recesses positioned between the staple openings of the inner annular array of staple openings, wherein at least some of the recesses of the inner plurality of recesses communicate with one another via at least one channel.

\* \* \* \* \*